US007267685B2

(12) United States Patent
Butaric et al.

(10) Patent No.: US 7,267,685 B2
(45) Date of Patent: Sep. 11, 2007

(54) BILATERAL EXTENSION PROSTHESIS AND METHOD OF DELIVERY

(75) Inventors: Frank Butaric, Pembroke Pines, FL (US); William L. Howat, Weston, FL (US); Robert P. Letendre, Hialeah, FL (US); Marc Ramer, Weston, FL (US); Kenneth S. Solovay, Weston, FL (US)

(73) Assignee: Cordis Corporation, Miami Lakes, FL (US)

( * ) Notice: Subject to any disclaimer, the term of this patent is extended or adjusted under 35 U.S.C. 154(b) by 374 days.

(21) Appl. No.: 10/041,373

(22) Filed: Jan. 8, 2002

(65) Prior Publication Data

US 2002/0058987 A1    May 16, 2002

Related U.S. Application Data

(63) Continuation-in-part of application No. 09/714,080, filed on Nov. 16, 2000, now Pat. No. 6,656,215, and a continuation-in-part of application No. 09/714,078, filed on Nov. 16, 2000, now Pat. No. 6,626,938, and a continuation-in-part of application No. 09/714,093, filed on Nov. 16, 2000, and a continuation-in-part of application No. 09/714,079, filed on Nov. 16, 2000, now Pat. No. 6,482,227.

(51) Int. Cl.
*A61F 2/06* (2006.01)
(52) U.S. Cl. .................... 623/1.16; 623/1.35
(58) Field of Classification Search ............. 623/1.13, 623/1.16, 1.35, 1.36, 1.34, 1.28
See application file for complete search history.

(56) References Cited

U.S. PATENT DOCUMENTS 3,585,707 A    6/1971  Stevens

| 3,657,744 A | 4/1972 | Ersek |
| 4,169,464 A | 10/1979 | Obrez |
| 4,187,390 A | 2/1980 | Gore |
| 4,317,451 A | 3/1982 | Cerwin et al. |
| 4,441,216 A | 4/1984 | Ionescu et al. |
| RE31,618 E | 7/1984 | Mano |
| 4,503,569 A | 3/1985 | Dotter |
| 4,553,545 A | 11/1985 | Maass |
| 4,562,596 A | 1/1986 | Kornberg |

(Continued)

FOREIGN PATENT DOCUMENTS

CA    2302638 A1    9/1997

(Continued)

OTHER PUBLICATIONS

Kato Masaaki, Matsuda Takehisa, Kaneko Mitsunori.: "Experimental Assessment of Newly Devised Transcatheter Stent-Graft for Aortic Dissection" The Annals of Thoracic Surgery, vol. 59, No. 4, 1995, pp. 908-915, XP001152688, p. 909, paragraph 2-p. 911, paragraph 3, figure 2.

*Primary Examiner*—Corrine McDermott
*Assistant Examiner*—Cheryl Miller

(57) ABSTRACT

The invention is a system, apparatus, and method for treating, and/or repairing an aneurysm, preferably an aortic aneurysm, and most preferably, an abdominal aortic aneurysm. The systems, devices, and methods of the present invention include a prosthesis assembly for establishing a fluid flow path between an upstream portion of an artery and at least one bifurcated downstream portion of the artery.

1 Claim, 17 Drawing Sheets

U.S. PATENT DOCUMENTS

| | | |
|---|---|---|
| 4,580,568 A | 4/1986 | Gianturco |
| 4,604,762 A | 8/1986 | Robinson |
| 4,617,932 A | 10/1986 | Kornberg |
| 4,655,771 A | 4/1987 | Wallsten |
| 4,665,906 A | 5/1987 | Jervis |
| 4,681,110 A | 7/1987 | Wiktor |
| 4,705,517 A | 11/1987 | DiPisa, Jr. |
| 4,728,328 A | 3/1988 | Hughes |
| 4,731,073 A | 3/1988 | Robinson |
| 4,732,152 A | 3/1988 | Wallsten |
| 4,733,665 A | 3/1988 | Palmaz |
| 4,739,762 A | 4/1988 | Palmaz |
| 4,769,029 A | 9/1988 | Patel |
| 4,776,337 A | 10/1988 | Palmaz |
| 4,784,137 A | 11/1988 | Kulik et al. |
| 4,787,899 A | 11/1988 | Lazarus |
| 4,800,882 A | 1/1989 | Gianturco |
| 4,822,341 A | 4/1989 | Colone |
| 4,850,999 A | 7/1989 | Planck |
| 4,856,516 A | 8/1989 | Hillstead |
| 4,875,480 A | 10/1989 | Imbert |
| 4,886,062 A | 12/1989 | Wiktor |
| 4,907,336 A | 3/1990 | Gianturco |
| 4,913,141 A | 4/1990 | Hillstead |
| 4,921,495 A | 5/1990 | Kira |
| 4,925,445 A | 5/1990 | Sakamoto |
| 4,950,227 A | 8/1990 | Savin |
| 4,955,899 A | 9/1990 | Della Corna |
| 4,969,458 A | 11/1990 | Wiktor |
| 4,990,131 A | 2/1991 | Dardik |
| 4,990,151 A | 2/1991 | Wallsten |
| 4,990,155 A | 2/1991 | Wilkoff |
| 4,994,071 A | 2/1991 | MacGregor |
| 5,015,253 A | 5/1991 | MacGregor |
| 5,019,085 A | 5/1991 | Hillstead |
| 5,026,377 A | 6/1991 | Burton |
| 5,035,694 A | 7/1991 | Kasprzyk et al. |
| 5,035,706 A | 7/1991 | Giantureo |
| 5,041,126 A | 8/1991 | Gianturco |
| 5,045,072 A | 9/1991 | Castillo |
| 5,064,435 A | 11/1991 | Porter |
| 5,078,726 A | 1/1992 | Kreamer |
| 5,084,065 A | 1/1992 | Weldon |
| 5,100,422 A | 3/1992 | Berguer |
| 5,102,417 A | 4/1992 | Palmaz |
| 5,104,399 A | 4/1992 | Lazarus |
| 5,104,400 A | 4/1992 | Berguer |
| 5,104,404 A | 4/1992 | Wolff |
| 5,114,423 A | 5/1992 | Kasprzyk et al. |
| 5,116,365 A | 5/1992 | Hillstead |
| 5,122,154 A | 6/1992 | Rhodes |
| 5,123,917 A | 6/1992 | Lee |
| 5,131,908 A | 7/1992 | Dardik et al. |
| 5,133,732 A | 7/1992 | Wiktor |
| 5,135,536 A | 8/1992 | Hillstead |
| 5,151,105 A | 9/1992 | Kwan-Gett |
| 5,152,782 A | 10/1992 | Kowligi |
| 5,156,620 A | 10/1992 | Pigott |
| 5,159,920 A | 11/1992 | Condon |
| 5,163,951 A | 11/1992 | Pinchuk |
| 5,163,958 A | 11/1992 | Pinchuk |
| 5,171,262 A | 12/1992 | MacGregor |
| 5,176,660 A | 1/1993 | Truckai |
| 5,178,618 A | 1/1993 | Kandarpa |
| 5,192,297 A | 3/1993 | Hull |
| 5,192,307 A | 3/1993 | Wall |
| 5,195,984 A | 3/1993 | Schatz |
| 5,207,695 A | 5/1993 | Trout, III |
| 5,211,658 A | 5/1993 | Clouse |
| 5,217,483 A | 6/1993 | Tower |
| 5,219,355 A | 6/1993 | Parodi |
| 5,222,971 A | 6/1993 | Willard et al. |
| 5,236,447 A | 8/1993 | Kubo |
| 5,246,445 A | 9/1993 | Yachia et al. |
| 5,246,452 A | 9/1993 | Sinnott |
| 5,254,107 A | 10/1993 | Soltesz |
| 5,258,021 A | 11/1993 | Duran |
| 5,258,027 A | 11/1993 | Berghaus |
| 5,266,073 A | 11/1993 | Wall |
| 5,275,622 A | 1/1994 | Lazarus et al. |
| 5,282,823 A | 2/1994 | Schwartz et al. |
| 5,282,824 A | 2/1994 | Gianturco |
| 5,282,847 A | 2/1994 | Trescony et al. |
| 5,282,860 A | 2/1994 | Matsuno |
| 5,290,305 A | 3/1994 | Inoue |
| 5,292,331 A | 3/1994 | Boneau |
| 5,304,197 A | 4/1994 | Pinchuk |
| 5,304,200 A | 4/1994 | Spaulding |
| 5,306,294 A | 4/1994 | Winston |
| 5,314,444 A | 5/1994 | Gianturco |
| 5,314,472 A | 5/1994 | Fontaine |
| 5,316,023 A | 5/1994 | Palmaz |
| 5,318,535 A | 6/1994 | Miraki |
| 5,321,109 A | 6/1994 | Bosse |
| 5,330,490 A | 7/1994 | Wilk |
| 5,330,500 A | 7/1994 | Song |
| 5,330,528 A | 7/1994 | Lazim |
| 5,334,201 A | 8/1994 | Cowan |
| 5,334,301 A | 8/1994 | Heinke et al. |
| 5,342,387 A | 8/1994 | Summersq |
| 5,354,257 A | 10/1994 | Roubin et al. |
| 5,354,308 A | 10/1994 | Simon et al. |
| 5,358,493 A | 10/1994 | Schweich, Jr. et al. |
| 5,360,443 A | 11/1994 | Barone |
| 5,366,473 A | 11/1994 | Winston |
| 5,366,504 A | 11/1994 | Andersen et al. |
| 5,370,683 A | 12/1994 | Fontaine |
| 5,370,691 A | 12/1994 | Samson |
| 5,375,612 A | 12/1994 | Cottenceau et al. |
| 5,376,112 A | 12/1994 | Duran |
| 5,380,328 A | 1/1995 | Morgan |
| 5,382,261 A | 1/1995 | Palmaz |
| 5,383,927 A | 1/1995 | DeGoicoechea |
| 5,387,235 A | 2/1995 | Chuter |
| 5,389,106 A | 2/1995 | Tower |
| 5,395,390 A | 3/1995 | Simon et al. |
| 5,397,345 A | 3/1995 | Lazarus |
| 5,397,355 A | 3/1995 | Marin et al. |
| 5,403,341 A | 4/1995 | Solar |
| 5,405,322 A | 4/1995 | Lennox et al. |
| 5,405,377 A | 4/1995 | Cragg |
| 5,411,507 A | 5/1995 | Heckele |
| 5,411,549 A | 5/1995 | Peters |
| 5,417,708 A | 5/1995 | Hall et al. |
| 5,419,324 A | 5/1995 | Dillow |
| D359,802 S | 6/1995 | Fontaine |
| 5,421,955 A | 6/1995 | Lau et al. |
| 5,423,885 A | 6/1995 | Williams |
| 5,439,446 A | 8/1995 | Barry |
| 5,441,515 A | 8/1995 | Khosravi et al. |
| 5,441,516 A | 8/1995 | Wang et al. |
| 5,443,477 A | 8/1995 | Marin et al. |
| 5,443,496 A | 8/1995 | Schwartz et al. |
| 5,443,498 A | 8/1995 | Fontaine |
| 5,443,500 A | 8/1995 | Sigwart |
| 5,449,372 A | 9/1995 | Schmaltz et al. |
| 5,449,373 A | 9/1995 | Pinchasik et al. |
| 5,449,382 A | 9/1995 | Dayton |
| 5,453,090 A | 9/1995 | Martinez et al. |
| 5,453,235 A | 9/1995 | Calcote |
| 5,456,713 A | 10/1995 | Chuter |
| 5,466,509 A | 11/1995 | Kowligi |
| 5,468,138 A | 11/1995 | Bosse |
| 5,476,506 A | 12/1995 | Lunn |

| | | |
|---|---|---|
| 5,480,423 A | 1/1996 | Ravenscroft |
| 5,484,444 A | 1/1996 | Braunschweiler |
| 5,489,295 A | 2/1996 | Piplani et al. |
| 5,496,365 A | 3/1996 | Sgro |
| 5,507,767 A | 4/1996 | Maeda et al. |
| 5,507,769 A | 4/1996 | Marin |
| 5,507,771 A | 4/1996 | Gianturco |
| 5,507,995 A | 4/1996 | Schweich, Jr. et al. |
| 5,512,229 A | 4/1996 | Bosse |
| 5,522,880 A | 6/1996 | Barone |
| 5,522,882 A | 6/1996 | Gaterud |
| 5,527,354 A | 6/1996 | Fontaine et al. |
| 5,549,662 A | 8/1996 | Fordenbacher |
| 5,549,663 A | 8/1996 | Cottone, Jr. |
| 5,562,698 A | 10/1996 | Parker |
| 5,562,724 A | 10/1996 | Vorwerk |
| 5,562,726 A | 10/1996 | Chuter |
| 5,569,295 A | 10/1996 | Lam |
| 5,571,170 A | 11/1996 | Palmaz |
| 5,571,171 A | 11/1996 | Barone |
| 5,571,173 A | 11/1996 | Parodi |
| 5,578,071 A | 11/1996 | Parodi |
| 5,578,072 A | 11/1996 | Barone |
| 5,591,196 A | 1/1997 | Marin et al. |
| 5,591,197 A | 1/1997 | Orth et al. |
| 5,591,228 A | 1/1997 | Edoga |
| 5,591,229 A | 1/1997 | Parodi |
| 5,593,412 A | 1/1997 | Martinez et al. |
| 5,607,444 A | 3/1997 | Lam |
| 5,607,464 A | 3/1997 | Trescony et al. |
| 5,609,624 A | 3/1997 | Kalis |
| 5,609,625 A | 3/1997 | Piplani et al. |
| 5,609,627 A | 3/1997 | Goicoechea et al. |
| 5,617,878 A | 4/1997 | Taheri |
| 5,618,300 A | 4/1997 | Marin et al. |
| 5,628,783 A | 5/1997 | Quiachon et al. |
| 5,628,786 A | 5/1997 | Banas |
| 5,628,788 A | 5/1997 | Pinchuk |
| 5,632,763 A | 5/1997 | Glastra |
| 5,632,778 A | 5/1997 | Goldstein |
| 5,639,278 A | 6/1997 | Dereume et al. |
| 5,641,443 A | 6/1997 | Calcote |
| 5,643,312 A | 7/1997 | Fischell et al. |
| 5,645,559 A | 7/1997 | Hachtman |
| 5,649,952 A | 7/1997 | Lam |
| 5,653,743 A | 8/1997 | Martin |
| 5,653,745 A | 8/1997 | Trescony et al. |
| 5,653,747 A | 8/1997 | Dereume |
| 5,662,700 A | 9/1997 | Lazarus |
| 5,662,703 A | 9/1997 | Yurek et al. |
| 5,667,523 A | 9/1997 | Bynon |
| 5,669,924 A | 9/1997 | Shaknovich |
| 5,669,936 A | 9/1997 | Lazarus |
| 5,674,241 A | 10/1997 | Bley |
| 5,674,276 A | 10/1997 | Andersen et al. |
| 5,676,696 A | 10/1997 | Marcade |
| 5,676,697 A | 10/1997 | McDonald |
| 5,681,345 A | 10/1997 | Euteneuer |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,685,847 A | 11/1997 | Barry |
| 5,693,083 A | 12/1997 | Baker et al. |
| 5,693,084 A | 12/1997 | Chuter |
| 5,693,085 A | 12/1997 | Buirge et al. |
| 5,693,086 A | 12/1997 | Goicoechea et al. |
| 5,695,517 A | 12/1997 | Marin et al. |
| 5,697,948 A | 12/1997 | Marin et al. |
| 5,697,971 A | 12/1997 | Fischell et al. |
| 5,700,285 A | 12/1997 | Myers |
| 5,702,418 A | 12/1997 | Ravenscroft |
| 5,713,917 A | 2/1998 | Leonhardt et al. |
| 5,716,365 A | 2/1998 | Goicoechea et al. |
| 5,718,159 A | 2/1998 | Thompson |
| 5,718,724 A | 2/1998 | Goicoechea et al. |
| 5,720,735 A | 2/1998 | Dorros |
| 5,720,776 A | 2/1998 | Chuter et al. |
| 5,723,003 A | 3/1998 | Winston |
| 5,723,004 A | 3/1998 | Dereume et al. |
| 5,725,534 A | 3/1998 | Rasmussen |
| 5,725,568 A | 3/1998 | Hastings |
| 5,725,570 A | 3/1998 | Heath |
| 5,728,065 A | 3/1998 | Follmer et al. |
| 5,728,068 A | 3/1998 | Leone et al. |
| 5,728,131 A | 3/1998 | Frantzen |
| 5,733,328 A | 3/1998 | Fordenbacher |
| 5,735,892 A | 4/1998 | Myers |
| 5,746,709 A | 5/1998 | Rom et al. |
| 5,749,880 A | 5/1998 | Banas |
| 5,749,920 A | 5/1998 | Quiachon et al. |
| 5,749,921 A | 5/1998 | Lenker et al. |
| 5,752,966 A | 5/1998 | Chang |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,772 A | 5/1998 | Evans et al. |
| 5,755,773 A | 5/1998 | Evans et al. |
| 5,755,777 A | 5/1998 | Chuter |
| 5,758,562 A | 6/1998 | Thompson |
| 5,760,006 A | 6/1998 | Shank |
| 5,766,201 A | 6/1998 | Ravenscroft et al. |
| 5,769,882 A | 6/1998 | Fogarty et al. |
| 5,769,885 A | 6/1998 | Quiachon et al. |
| 5,776,180 A | 7/1998 | Goicoechea et al. |
| 5,782,765 A | 7/1998 | Jonkman |
| 5,782,906 A | 7/1998 | Marshall et al. |
| 5,782,909 A | 7/1998 | Quiachon et al. |
| 5,788,626 A | 8/1998 | Thompson |
| 5,797,953 A | 8/1998 | Tekulve |
| 5,800,456 A | 9/1998 | Maeda et al. |
| 5,800,508 A | 9/1998 | Goicoechea et al. |
| 5,800,516 A | 9/1998 | Fine et al. |
| 5,800,518 A | 9/1998 | Piplani et al. |
| 5,800,520 A | 9/1998 | Fogarty et al. |
| 5,810,870 A | 9/1998 | Myers |
| 5,824,036 A | 10/1998 | Lauterjung |
| 5,824,037 A | 10/1998 | Fogarty et al. |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,043 A | 10/1998 | Cottone, Jr. |
| 5,824,044 A | 10/1998 | Quiachon et al. |
| 5,824,046 A | 10/1998 | Smith |
| 5,824,054 A | 10/1998 | Khosravi |
| 5,824,055 A | 10/1998 | Spiridigliozzi |
| 5,827,310 A | 10/1998 | Marin et al. |
| 5,827,320 A | 10/1998 | Richter et al. |
| 5,827,327 A | 10/1998 | McHaney |
| 5,830,229 A | 11/1998 | Konya et al. |
| 5,833,651 A | 11/1998 | Donovan et al. |
| 5,840,011 A | 11/1998 | Landgrebe et al. |
| 5,843,031 A | 12/1998 | Hermann et al. |
| 5,843,120 A | 12/1998 | Israel |
| 5,843,158 A | 12/1998 | Lenker et al. |
| 5,843,160 A | 12/1998 | Rhodes |
| 5,855,598 A | 1/1999 | Pinchuk |
| 5,857,998 A | 1/1999 | Barry |
| 5,858,556 A | 1/1999 | Eckert |
| 5,860,998 A | 1/1999 | Robinson et al. |
| 5,861,027 A | 1/1999 | Trapp |
| 5,868,777 A | 2/1999 | Lam |
| 5,871,537 A | 2/1999 | Holman et al. |

| | | |
|---|---|---|
| 5,871,538 A | 2/1999 | Dereume |
| 5,876,397 A | 3/1999 | Edelman et al. |
| 5,893,868 A | 4/1999 | Hanson et al. |
| 5,893,887 A | 4/1999 | Jayaraman |
| 5,899,890 A | 5/1999 | Chiang et al. |
| 5,902,308 A | 5/1999 | Murphy |
| 5,904,713 A | 5/1999 | Leschinsky |
| 5,906,619 A | 5/1999 | Olson et al. |
| 5,906,640 A | 5/1999 | Penn et al. |
| 5,906,641 A | 5/1999 | Thompson et al. |
| 5,908,448 A | 6/1999 | Roberts et al. |
| 5,916,263 A | 6/1999 | Goicoechea et al. |
| 5,916,264 A | 6/1999 | Von Oepen |
| 5,919,224 A | 7/1999 | Thompson et al. |
| 5,928,260 A | 7/1999 | Chin et al. |
| 5,935,667 A | 8/1999 | Calcote |
| 5,938,696 A | 8/1999 | Goicoechea et al. |
| 5,944,726 A | 8/1999 | Blaeser et al. |
| 5,944,750 A | 8/1999 | Tanner et al. |
| 5,951,599 A | 9/1999 | McCrory |
| 5,954,693 A | 9/1999 | Barry |
| 5,957,973 A | 9/1999 | Quiachon et al. |
| 5,957,974 A | 9/1999 | Thompson et al. |
| 5,961,548 A | 10/1999 | Shmulewitz |
| 5,968,069 A | 10/1999 | Dusbabek et al. |
| 5,968,088 A | 10/1999 | Hansen et al. |
| 5,980,565 A | 11/1999 | Jayaraman |
| 5,993,481 A | 11/1999 | Marcade et al. |
| 6,007,543 A | 12/1999 | Ellis et al. |
| 6,015,431 A | 1/2000 | Thornton et al. |
| 6,015,432 A | 1/2000 | Rakos et al. |
| 6,016,810 A | 1/2000 | Ravenscroft |
| 6,017,363 A | 1/2000 | Hojeibane |
| 6,017,364 A | 1/2000 | Lazarus |
| 6,019,778 A | 2/2000 | Wilson |
| 6,019,786 A | 2/2000 | Thompson |
| 6,024,763 A | 2/2000 | Lenker et al. |
| 6,027,526 A | 2/2000 | Limon et al. |
| 6,027,529 A | 2/2000 | Roychowdhury et al. |
| 6,030,413 A | 2/2000 | Lazarus |
| 6,030,415 A | 2/2000 | Chuter |
| 6,033,435 A | 3/2000 | Penn et al. |
| 6,036,697 A | 3/2000 | DiCaprio |
| 6,036,723 A | 3/2000 | Anidjar et al. |
| 6,036,725 A | 3/2000 | Avellanet |
| 6,039,749 A | 3/2000 | Marin et al. |
| 6,039,758 A | 3/2000 | Quiachon et al. |
| 6,048,356 A | 4/2000 | Ravenscroft et al. |
| 6,051,020 A | 4/2000 | Goicoechea et al. |
| 6,056,775 A | 5/2000 | Borghi et al. |
| 6,059,821 A | 5/2000 | Anidjar et al. |
| 6,059,823 A | 5/2000 | Holman et al. |
| 6,059,824 A | 5/2000 | Taheri |
| 6,063,111 A | 5/2000 | Hieshima et al. |
| 6,068,655 A | 5/2000 | Seguin et al. |
| 6,070,589 A | 6/2000 | Keith et al. |
| 6,077,273 A | 6/2000 | Euteneuer et al. |
| 6,078,832 A | 6/2000 | Lenker et al. |
| 6,086,577 A | 7/2000 | Ken et al. |
| 6,086,611 A | 7/2000 | Duffy et al. |
| 6,090,127 A | 7/2000 | Globerman |
| 6,090,128 A | 7/2000 | Douglas |
| 6,090,133 A | 7/2000 | Richter et al. |
| 6,093,199 A | 7/2000 | Brown et al. |
| 6,097,978 A | 8/2000 | Demarais et al. |
| 6,099,558 A | 8/2000 | White et al. |
| 6,099,560 A | 8/2000 | Penn et al. |
| 6,102,938 A | 8/2000 | Evans et al. |
| 6,102,940 A * | 8/2000 | Robichon et al. .......... 623/1.35 |
| 6,102,942 A | 8/2000 | Ahari |
| 6,110,191 A | 8/2000 | Dehdashtian et al. |
| 6,110,198 A | 8/2000 | Fogarty et al. |
| 6,117,117 A | 9/2000 | Mauch |
| 6,117,156 A | 9/2000 | Richter et al. |
| 6,117,157 A | 9/2000 | Tekulve |
| 6,117,167 A | 9/2000 | Goicoechea et al. |
| 6,123,722 A | 9/2000 | Fogarty et al. |
| 6,126,685 A | 10/2000 | Lenker et al. |
| 6,129,754 A | 10/2000 | Kanesaka et al. |
| 6,129,756 A | 10/2000 | Kugler et al. |
| 6,132,450 A | 10/2000 | Hanson et al. |
| 6,132,459 A | 10/2000 | Piplani et al. |
| 6,193,745 B1 * | 2/2001 | Fogarty et al. ............. 326/1.12 |
| 6,302,906 B1 | 10/2001 | Goicoechea et al. |
| 6,306,164 B1 | 10/2001 | Kujawski |
| 6,325,819 B1 | 12/2001 | Pavcnik et al. |
| 6,325,823 B1 * | 12/2001 | Horzewski et al. ........ 623/1.16 |
| 6,485,524 B2 * | 11/2002 | Strecker ..................... 623/1.15 |
| 6,524,336 B1 * | 2/2003 | Papazolgou et al. ....... 623/1.35 |
| 6,994,722 B2 * | 2/2006 | DiCarlo ..................... 623/1.13 |
| 7,029,496 B2 * | 4/2006 | Rakos et al. ................ 623/1.35 |
| 2002/0198585 A1 | 12/2002 | Wisselink |
| 2003/0120330 A1 * | 6/2003 | Ouriel et al. ............... 623/1.12 |
| 2003/0120333 A1 * | 6/2003 | Ouriel et al. ............... 623/1.14 |

FOREIGN PATENT DOCUMENTS

| | | |
|---|---|---|
| DE | D3205942 A1 | 9/1983 |
| EP | 0293090 A | 11/1988 |
| EP | 0 540 290 A3 | 5/1993 |
| EP | 0579523 A1 | 1/1994 |
| EP | 0657147 A2 | 10/1994 |
| EP | 0686379 B1 | 12/1995 |
| EP | 734698 A2 | 10/1996 |
| EP | 783873 A2 | 7/1997 |
| EP | 800801 A1 | 10/1997 |
| EP | 830853 A1 | 3/1998 |
| EP | 832616 A1 | 4/1998 |
| EP | 0855170 A2 | 7/1998 |
| EP | 880948 A1 | 12/1998 |
| EP | 0928606 A1 | 7/1999 |
| EP | 937442 A2 | 8/1999 |
| EP | 0947179 A2 | 10/1999 |
| EP | 1000590 A1 | 5/2000 |
| EP | 0667132 B1 | 11/2001 |
| EP | 121989 A2 | 6/2002 |
| EP | 1086665 B1 | 3/2005 |
| FR | 0 566 807 A1 | 2/1924 |
| FR | 2733682 A1 | 11/1996 |
| FR | 2740346 A1 | 4/1997 |
| FR | 2743293 A1 | 7/1997 |
| GB | 0 662 307 A2 | 9/1948 |
| GB | 1 205 743 | 9/1970 |
| JP | 5524095 A | 2/1980 |
| JP | 60220030 A | 11/1985 |
| JP | 62231657 A | 3/1988 |
| JP | 464367 A | 2/1992 |
| JP | 4263852 A | 4/1992 |
| JP | 5 76603 A | 3/1993 |
| JP | 5 269199 A | 10/1993 |
| JP | 7529 A | 10/1994 |
| JP | 6282730 A | 10/1994 |
| JP | 7 24072 A | 1/1995 |
| JP | 7100210 A | 4/1995 |
| JP | 8-196643 | 8/1996 |
| JP | 6 86827 A | 6/1998 |
| SU | 1680055 | 5/1988 |
| WO | 8704935 A1 | 8/1987 |
| WO | 9516406 A1 | 6/1995 |
| WO | 9521592 A1 | 8/1995 |
| WO | 9626689 A1 | 9/1996 |
| WO | 96/34580 A1 | 11/1996 |
| WO | 9724081 A1 | 7/1997 |
| WO | 9725000 A1 | 7/1997 |
| WO | 9733532 A2 | 9/1997 |
| WO | 9807389 A1 | 2/1998 |

| WO | 98/19628 | A1 | 5/1998 | WO | 9908744 | A1 | 2/1999 |
| WO | 9823322 | A1 | 6/1998 | WO | 9911199 | A1 | 3/1999 |
| WO | 9836709 | A1 | 8/1998 | | | | |
| WO | 9853761 | A1 | 12/1998 | * cited by examiner | | | |

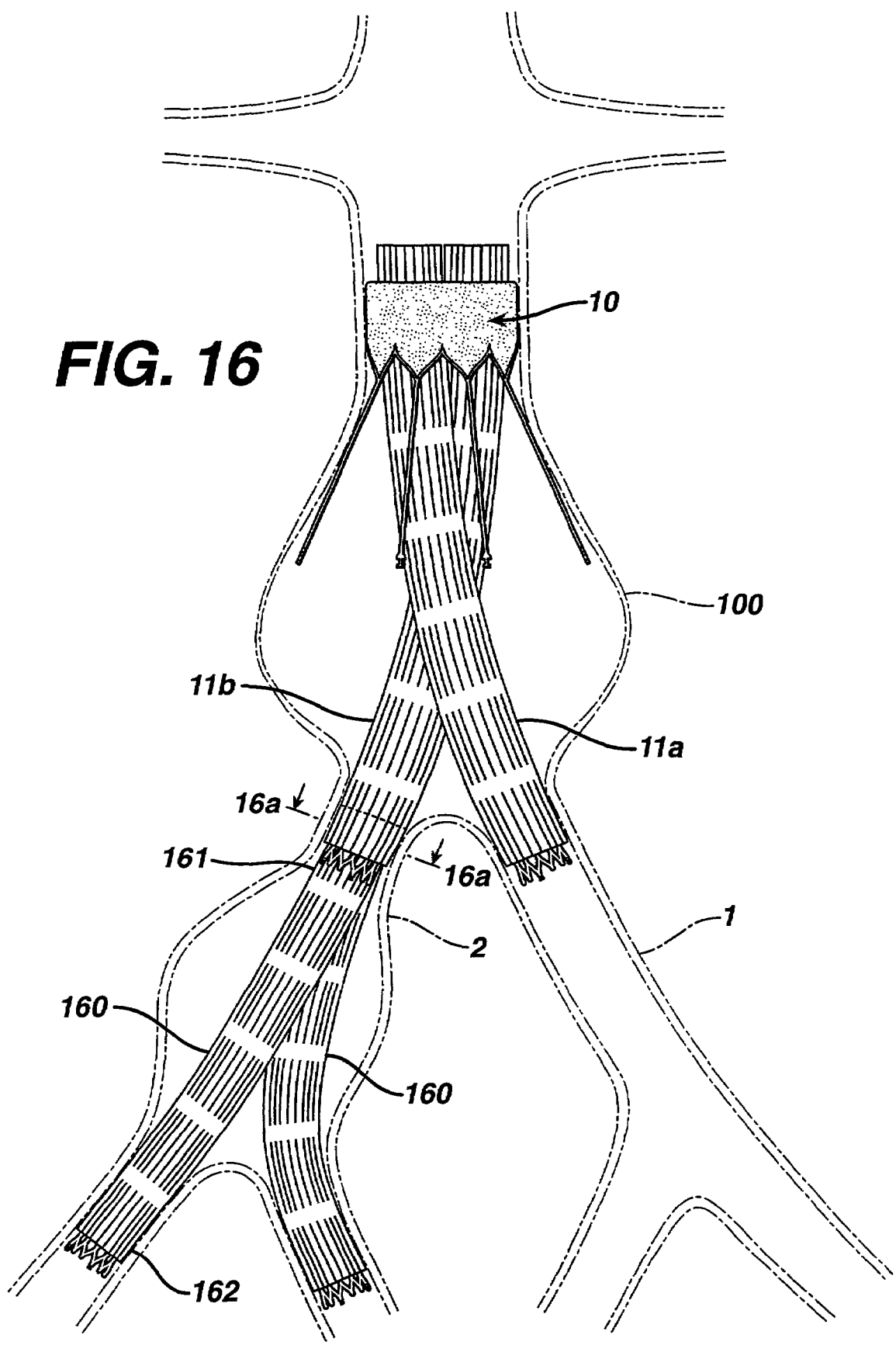

BILATERAL EXTENSION PROSTHESIS AND METHOD OF DELIVERY

CROSS-REFERENCE TO RELATED APPLICATIONS

This application is a continuation in part of U.S. application Ser. No. 09/714,080, filed on Nov. 16,2000 now U.S. Pat. No. 6,656,215; U.S. application Ser. No. 09/714,078, filed on Nov. 16, 2000 Now U.S. Pat. No. 6,626,938; U.S. application Ser. No. 09/714,093, filed on Nov. 16, 2000 and U.S. application Ser. No. 09/714,079, filed on Nov. 16, 2000 now U.S. Pat. No 6,482,227.

BACKGROUND OF THE INVENTION

1. Field of the Invention

The present invention relates to devices and methods for repairing aneurysms, and more particularly, to percutaneously and/or intraluminally delivered devices and methods for repairing aneurysms, such as abdominal aortic aneurysms and thoracic aortic aneurysms.

2. Discussion of the Related Art

An aneurysm is an abnormal dilation of a layer or layers of an arterial wall, usually caused by a systemic collagen synthetic or structural defect. An abdominal aortic aneurysm is an aneurysm in the abdominal portion of the aorta, usually located in or near one or both of the two iliac arteries or near the renal arteries. The aneurysm often arises in the infrarenal portion of the diseased aorta, for example, below the kidneys. A thoracic aortic aneurysm is an aneurysm in the thoracic portion of the aorta. When left untreated, the aneurysm may rupture, usually causing rapid fatal hemorrhaging.

Aneurysms may be classified or typed by their position as well as by the number of aneurysms in a cluster. Typically, abdominal aortic aneurysms may be classified into five types. A Type I aneurysm is a single dilation located between the renal arteries and the iliac arteries. Typically, in a Type I aneurysm, the aorta is healthy between the renal arteries and the aneurysm and between the aneurysm and the iliac arteries.

A Type II A aneurysm is a single dilation located between the renal arteries and the iliac arteries. In a Type II A aneurysm, the aorta is healthy between the renal arteries and the aneurysm, but not healthy between the aneurysm and the iliac arteries. In other words, the dilation extends to the aortic bifurcation. A Type II B aneurysm comprises three dilations. One dilation is located between the renal arteries and the iliac arteries. Like a Type II A aneurysm, the aorta is healthy between the aneurysm and the renal arteries, but not healthy between the aneurysm and the iliac arteries. The other two dilations are located in the iliac arteries between the aortic bifurcation and the bifurcations between the external iliacs and the internal iliacs. The iliac arteries are healthy between the iliac bifurcation and the aneurysms. A Type II C aneurysm also comprises three dilations. However, in a Type II C aneurysm, the dilations in the iliac arteries extend to the iliac bifurcation.

A Type III aneurysm is a single dilation located between the renal arteries and the iliac arteries. In a Type III aneurysm, the aorta is not healthy between the renal arteries and the aneurysm. In other words, the dilation extends to the renal arteries.

A ruptured abdominal aortic aneurysm is presently the thirteenth leading cause of death in the United States. The routine management of abdominal aortic aneurysms has been surgical bypass, with the placement of a graft in the involved or dilated segment. Although resection with a synthetic graft via transperitoneal or retroperitoneal procedure has been the standard treatment, it is associated with significant risk. For example, complications include perioperative myocardial ischemia, renal failure, erectile impotence, intestinal ischemia, infection, lower limb ischemia, spinal cord injury with paralysis, aorta-enteric fistula, and death. Surgical treatment of abdominal aortic aneurysms is associated with an overall mortality rate of five percent in asymptomatic patients, sixteen to nineteen percent in symptomatic patients, and is as high as fifty percent in patients with ruptured abdominal aortic aneurysms.

Disadvantages associated with conventional surgery, in addition to the high mortality rate, include an extended recovery period associated with the large surgical incision and the opening of the abdominal cavity, difficulties in suturing the graft to the aorta, the loss of the existing thrombosis to support and reinforce the graft, the unsuitability of the surgery for many patients having abdominal aortic aneurysms, and the problems associated with performing the surgery on an emergency basis after the aneurysm has ruptured. Further, the typical recovery period is from one to two weeks in the hospital and a convalescence period at home from two to three months or more, if complications ensue. Since many patients having abdominal aortic aneurysms have other chronic illnesses, such as heart, lung, liver and/or kidney disease, coupled with the fact that many of these patients are older, they are less than ideal candidates for surgery.

The occurrence of aneurysms is not confined to the abdominal region. While abdominal aortic aneurysms are generally the most common, aneurysms in other regions of the aorta or one of its branches are possible. For example, aneurysms may occur in the thoracic aorta. As is the case with abdominal aortic aneurysms, the widely accepted approach to treating an aneurysm in the thoracic aorta is surgical repair, involving replacing the aneurysmal segment with a prosthetic device. This surgery, as described above, is a major undertaking, with associated high risks and with significant mortality and morbidity.

Over the past five years, there has been a great deal of research directed at developing less invasive, endovascular, i.e. catheter directed, techniques for the treatment of aneurysms, specifically abdominal aortic aneurysms. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

Stent-grafts or endoprostheses are now FDA approved and commercially available. Their delivery procedure typically involves advanced angiographic techniques performed through vascular accesses gained via surgical cutdown of a remote artery, which may include the common femoral or brachial arteries. Over a guidewire, the appropriate size introducer will be placed. The catheter and guidewire are passed the aneurysm. Through the introducer, the stent-graft will be advanced to the appropriate position. Typical deployment of the stent-graft device requires withdrawal of an outer sheath while maintaining the position of the stent-graft with an inner-stabilizing device. Most stent-grafts are self-expanding; however, an additional angioplasty procedure, e.g., balloon angioplasty, may be required to secure the position of the stent-graft. Following the placement of the stent-graft, standard angiographic views may be obtained.

Due to the large diameter of the above-described devices, typically greater than twenty French (3F=1 mm), arteriotomy closure typically requires open surgical repair. Some procedures may require additional surgical techniques, such as hypogastric artery embolization, vessel ligation, or surgical bypass, in order to adequately treat the aneurysm or to maintain flow to both lower extremities. Likewise, some procedures will require additional, advanced catheter directed techniques, such as angioplasty, stent placement, and embolization, in order to successfully exclude the aneurysm and efficiently manage leaks.

While the above-described endoprostheses represent a significant improvement over conventional surgical techniques, there is a need to improve the endoprostheses, their method of use and their applicability to varied biological conditions. Accordingly, in order to provide a safe and effective alternate means for treating aneurysms, including abdominal aortic aneurysms and thoracic aortic aneurysms, a number of difficulties associated with currently known endoprostheses and their delivery systems must be overcome. One concern with the use of endoprostheses is the prevention of endo-leaks and the disruption of the normal fluid dynamics of the vasculature. Devices using any technology should preferably be simple to position and reposition as necessary, should preferably provide an acute, fluid tight seal, and should preferably be anchored to prevent migration without interfering with normal blood flow in both the aneurysmal vessel as well as branching vessels. In addition, devices using the technology should preferably be able to be anchored, sealed, and maintained in bifurcated vessels, tortuous vessels, highly angulated vessels, partially diseased vessels, calcified vessels, odd shaped vessels, short vessels, and long vessels. In order to accomplish this, the endoprostheses should preferably be extendable and re-configurable while maintaining acute and long-term fluid tight seals and anchoring positions.

The endoprostheses should also preferably be able to be delivered percutaneously utilizing catheters, guidewires and other devices which substantially eliminate the need for open surgical intervention. Accordingly, the diameter of the endoprostheses in the catheter is an important factor. This is especially true for aneurysms in the larger vessels, such as the thoracic aorta.

SUMMARY OF THE INVENTION

The bilateral extension prosthesis of the present invention provides a means for overcoming the problems associated with anchoring and/or sealing a by-pass prosthesis in bifurcated sections of arteries as briefly described above.

The present invention is directed to a system including at least one prosthesis for repair or replacement of a mammalian body part or condition. The typical system includes a first prosthesis for sealing the system within a predetermined portion of an artery; at least one second prosthesis engaged to the first prosthesis, said second prosthesis providing a fluid flow path through the system or a portion of the system; and a third or extension prosthesis for extending a fluid flow path through the system or a portion of the system. In some embodiments of the invention, the second prosthesis is sealingly and/or matingly engaged with the first prosthesis. In some embodiments of the invention, the extension prosthesis extends the fluid flow path formed by the second prosthesis. In some embodiments of the invention, the extension prosthesis is sealingly and/or matingly engaged with the second prosthesis.

The present invention further comprises a first extension prosthesis configured to engage a proximal portion of said first bypass prosthesis, said first extension prosthesis configured with a distal portion positioned in a smaller arterial vessel, such as an external iliac artery. The present invention may further comprise a second extension prosthesis configured to engage a proximal portion of said first bypass prosthesis, said second extension prosthesis configured with a distal portion positioned in a smaller arterial vessel, such as an internal iliac artery.

A typical first prosthesis includes a support or stent structure, and a foam or gasket material supported by the stent, the stent and gasket material being configured to seal the system within an artery. A typical first prosthesis also includes one or more structures or elements for engaging the second prosthesis. In preferred embodiments of the invention, these elements or structures sealingly and/or matingly engage the second prosthesis. The stent is typically a synthetic or natural matrix for supporting the gasket material. In some exemplary embodiments of the stent, the stent is a hollow, substantially cylindrical, and preferably radially expandable matrix having a lumen and two open ends. The typical gasket material is a synthetic or natural fabric, tissue, foam, or the like. In preferred embodiments of the invention, the gasket material covers at least a portion of the lumen, even more preferably, the proximal end of the lumen.

The typical second prosthesis includes a support or stent structure, and graft material supported by the stent, the stent and graft material defining a fluid flow path therethrough. The typical graft material is a synthetic or natural fabric, tissue, or the like. The stent is typically a synthetic or natural matrix for supporting the graft and/or positioning the prosthesis in a pre-determined position. In some exemplary embodiments of the stent, the stent is a hollow, substantially cylindrical, and preferably radially expandable matrix having a lumen and two open ends. The stent typically comprises a plurality of interconnected struts. In some exemplary embodiments of the invention, a graft material may be positioned on an inside and/or outside surface of the matrix; in preferred embodiments of the invention, the graft material may include a plurality of substantially longitudinally directed pleats disposed thereon. In a particularly preferred embodiment, the graft further includes a plurality of radially oriented pleat interruptions. In some exemplary embodiments of the invention the graft material may be attached to the stent, preferably by one or more staples or the like.

A prosthesis according to the invention, typically a bypass prosthesis, may include, or may be configured to include, at least one gasket member positioned or placeable in a distal portion of said bypass prosthesis. In this exemplary embodiment of the invention, the gasket member may be adapted to receive one or more extension prostheses in a fluid tight arrangement.

Furthermore, a bypass prosthesis may be modified to provide bifurcated access to one or more downstream arteries. For example, a bypass prosthesis may be configured or include elements that permit delivery of one or more extension prostheses through or attached to the bypass prosthesis and into a downstream artery. Such an assembly permits placement of at least one prosthesis through a bifurcated portion of an arterial network. The engagement or interlocking elements may be incorporated into the bypass prosthesis design, or may be delivered to a distal portion of the bypass prosthesis in vivo. Such engagement elements form an interlocking communication at desired positions in the bypass prosthesis, preferably during in vivo assembly of a system according to the invention.

A system according to the present invention is intended for repairing or bypassing an aneurysm, preferably an aortic aneurysm. The system may also be used to direct fluid flow from one portion of a fluid pathway to another.

The accompanying figures show illustrative embodiments of the invention from which these and other of the objectives, novel features and advantages will be readily apparent.

BRIEF DESCRIPTION OF THE DRAWINGS

The foregoing and other aspects of the present invention will best be appreciated with reference to the detailed description of the invention in conjunction with the accompanying drawings. Throughout the figures and the description below, like numerals indicate the same element.

FIG. 16 is a perspective view of a system according to the invention having a bypass prosthesis and a first extension prosthesis that extends into a first iliac artery.

DETAILED DESCRIPTION OF THE PREFERRED EMBODIMENTS

Figure 1:
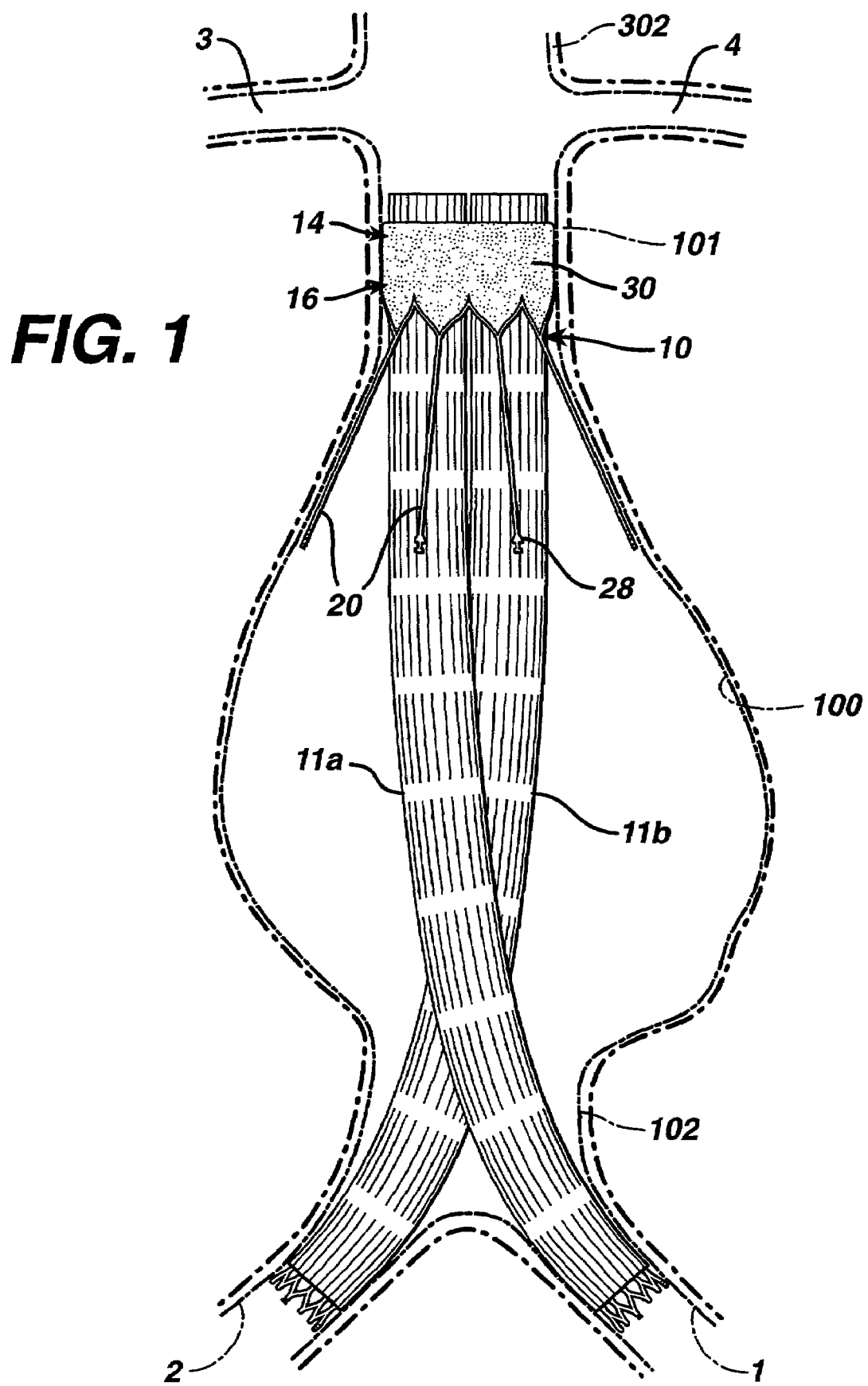
FIG. 1 is an elevation view of a fully deployed aortic repair system made in accordance with the present invention.

The apparatuses, systems, methods, and kits of the present invention may be used in the treatment of aortic aneurysms, preferably an abdominal aortic aneurysm, among other uses noted below. A better understanding of the present device and its use in treating aortic aneurysms will be achieved by reading the following description in conjunction with the above-incorporated references.

The present invention is directed to a system, apparatus, method, and their respective components for establishing a fluid path from one portion of an artery into a bifurcated or branched portion of a downstream portion of the arterial network.

A system of the present invention includes at least one bypass prosthesis and at least one extension prosthesis, said bypass prosthesis comprising an extension receptacle or anchor in distal portion thereof, said extension prosthesis having a proximal portion thereof adapted and configured to engage the extension receptacle. In the exemplary embodiments of the invention that include more than one extension prosthesis, the system further comprises an extension receptacle having a first portion adapted to receive a first extension prosthesis and a second portion adapted to receive a second extension prosthesis; said system further comprising a first extension prosthesis having a proximal portion adapted and configured to engage the first portion of the extension receptacle, and a second extension prosthesis having a proximal portion adapted and configured to engage the second portion of the extension receptacle.

A system according to the present invention may also include one or more gasket members configured to seal the communication path or channel between the extension receptacle and the extension prosthesis. The gasket member may be variously configured. In some exemplary embodiments of the invention, the gasket member may be a portion of the extension receptacle ringing the aperture. In some exemplary embodiments of the invention, the gasket member may comprise an external ring around a proximal portion of the extension prosthesis, the external ring being configured to sealingly engage the aperture of the extension receptacle. In other exemplary embodiments of the invention, the gasket member may comprise a separate ring configured to be positioned around a proximal portion of the extension prosthesis. The invention also contemplates the use of various combinations of these different gasket embodiments.

The present invention also comprises a system, apparatus, and method for bifurcating a single fluid flow path into two fluid flow paths.

The extension receptacle noted above for bifurcating the single fluid flow path comprises a generally annular member or the like that conforms to and establishes a fluid tight connection across a cross section of the bypass prosthesis. The annular member may include one or more apertures adapted and configured to receive a proximal portion of an extension prosthesis.

The present invention is also directed to a system for repairing an aneurysm, said system being variously configured and/or assembled using components described in more detail below. Typical systems according to this aspect of the invention may include one or more first prostheses or a sealing component, one or more second prostheses or a fluid flow component, and, optionally, one or more component receptacles, assemblies, or connectors for matingly engaging one component with another. Preferred embodiments of a system of the present invention include a sealing component matingly engaged to two fluid flow path components.

A method according to the present invention comprises providing a bypass prosthesis, and sealingly engaging at least one extension prosthesis in a distal portion of the bypass prosthesis. In preferred embodiments of the invention, a distal portion of the extension prosthesis may be positioned in a downstream artery, preferably an iliac artery. A method according to the present invention may include sequentially sealingly engaging a first extension prosthesis and a second extension prosthesis in a distal portion of the bypass prosthesis, and positioning the first extension prosthesis in a first downstream artery, such as an internal or first iliac artery, and positioning the second extension prosthesis in a second downstream artery, such as an external or second iliac artery.

The present invention also includes a delivery method for positioning a prosthesis in the internal iliac artery by means of a femoral, brachio-cephalic or radial introduction pathway. In these exemplary embodiments of the invention, a guide wire is passed through the bypass prosthesis proximally to distally, and into the internal iliac artery. A delivery catheter or the like comprising an extension prosthesis may then be passed over the guidewire, again proximally to distally, and into the internal iliac artery. The extension prosthesis may then be deployed, with the trailing or proximal end of the prosthesis matingly engaging a distal portion of the bypass prosthesis, as described above.

The delivery method may further comprise delivering a second extension prosthesis through a guidewire/catheter assembly that passes from the external iliac artery into the distal portion of the bypass prosthesis. In this exemplary embodiment of the invention the proximal or leading end of the prosthesis is matingly engaged to the distal portion of the bypass prosthesis, as described above.

In preferred embodiments of the invention, the method includes anchoring the system using the second prosthesis in its expanded configuration. The method may further include anchoring the most upstream portion of the system using the first portion of the stent, matrix, or first prosthesis.

The present invention is also directed to a kit that includes one or more of the following: a sterile or sterilizable enclosure; a first prosthesis; a first prosthesis in an individual sterile enclosure; a second prosthesis; a second prosthesis in an individual sterile enclosure; a third prosthesis; a third prosthesis in an individual sterile enclosure; a bypass prosthesis; a bypass prosthesis in an individual sterile enclosure; at least one extension prosthesis; at least one extension prosthesis in an individual sterile enclosure; a gasket member; a gasket member in an individual sterile enclosure; at least one suture; at least one staple; a collar or catheter tip assembly configured to engage and deliver a first prosthesis, a second prosthesis, and/or a third prosthesis; and at least one marker configured for placement on a first prosthesis, a second prosthesis, a third prosthesis, and/or portions thereof.

The present invention also includes a kit comprising a prosthesis according to the invention, preferably in a sterile or sterilizable enclosure.

A system or kit of the present invention may include one or more modular components. As used herein, a modular component is configured, or adapted to engage, or includes one or more structures that are intended to communicate with or engage a complementary structure on another modular component.

Embodiments of the invention may further include one or more bypass prostheses configured to matingly engage a first prosthesis, said bypass prosthesis comprising a graft material engaging a stent, the stent comprising a hollow matrix including a series of interconnected struts, the matrix being moveable from a first closed position to a second open position; the stent having at least one attachment structure or connector for matingly engaging at least one second complementary structure on the first prosthesis. In some exemplary embodiments of the invention, the prosthesis further comprises at least one marker. In preferred embodiments of the invention, the marker or markers are positioned on or formed as part of the stent.

The systems, methods, and prostheses of the present invention may be used to treat or repair Schumacher Type IIC AAA disease, preferably without the need for surgery, and/or without compromising peripheral flow.

Definition

As used herein, aortic aneurysm refers to any failure of a conduit, such as an aortic wall, typically characterized by an undesirable dilation of a portion of the artery, vessel malformation, or an occlusion. An exemplary use of a system and method of the present invention is to repair an aortic aneurysm, and the use of such term is not intended to limit the use of the structures or systems of the present invention to repair or replace other conduit failures. The system and structures of the present invention may be used to treat, repair, replace, or bypass any blood vessel (e.g., artery, vein, capillary); any fluid carrying vessel (e.g., lymphatic vessels); any organ or portion thereof that includes a blood or fluid vessel; or any junction between blood vessels, between fluid vessels, and between organs and blood vessels. In preferred embodiments of the invention, the system and structures are used to treat, repair, replace, or bypass an abdominal aortic aneurysm.

As used herein fluid pathway refers to any in vivo structure through which a biological fluid passes. A preferred fluid pathway is an artery. Fluid pathways include, but are not limited to channels formed by an artery, a vein, a capillary, lymph nodes and channels, and arteries, veins, and capillaries within an organ or organelle.

As used herein fluid or biological fluid refers to any fluid produced by an animal, including a human. Exemplary biological fluids include but are not limited to blood, oxygenated blood, de-oxygenated blood, gastric fluids, amniotic fluid, spinal fluid, and lymph. The preferred fluid is blood or oxygenated blood.

As used herein, conduit typically refers to any structure used to convey a biological fluid. The conduit may be formed of natural or synthetic materials, or combinations thereof. Exemplary conduits include but are not limited to an artery, a vein, a capillary, lymph nodes and channels, and arteries, veins, and capillaries within an organ or organelle.

As used herein, "biofusion" is a word coined by assignee referring to the ability of cells, proteins, fibrin, and other biological molecules to incorporate into the pore structure of a material, such as a foam or gasket material, or a graft material. It is believed that this feature promotes a long term stable biological interface that cannot be separated about six weeks after implantation.

The biofusion effect has many advantages. It has the potential to obviate late endo-leakage by preventing areas of non-organized clot from being displaced or recanalized. It is also believed that biofusion creates a connective tissue collar around the prosthesis that may prevent the aortic neck from dilating over time. Restricting neck dilation avoids leakage pathways and implant migration that can be caused by an insufficient fit with the aorta.

As used herein, adapted for communication, communicating, or similar terms refer to any means, structures, or methods for establishing an operational association between two elements of the system. Similarly, engaging, adapted to engage, or similar terms refer to means, structures, or methods for contacting a first component, structure, or portion thereof with a second component, structure, or portion thereof. Exemplary structures are shown in the Figures. Typically, all of these terms and phrases refer to at least one structure in or on a first component configured to engage a complementary structure in or on a second component, and the use of these inter-engaging features to link a first prosthesis or component with a second prosthesis or component. The engagement or communication may be matingly (e.g., permanent) and/or releasably (e.g., temporary). In preferred embodiments of the invention, communication or engagement may be fluid tight, substantially fluid tight, or fluid tight to an extent so as to not substantially compromise the intended function of the structure.

For example, a connector may be adapted to receive or connect to a complementary connector on another prosthesis. As used herein, connector refers to any structure used to form a joint or to join itself to another component or portion thereof. These connectors or connections establish a fluid flow path through various elements of the apparatus, assembly, or system. In a preferred embodiment of the invention, the system is intended to establish at least one fluid flow path through a vessel, conduit, organ, or portions thereof. Typical connections include but are not limited to mating connections, such as Luer-type, screw-type, friction-type, or connectors that are bonded together.

As used herein, distal is used in accordance with its ordinary dictionary definition, e.g., referring to a position farthest from the beginning; in human anatomy, this term is commonly equivalent to caudal or inferior. Proximal is used in accordance with its ordinary dictionary definition, e.g., referring to a position nearest the beginning; in human anatomy, this term is commonly equivalent to cranial or superior. The terms distal and proximal are intended to convey opposite ends or portions of a device, channel, element, or structure. In relation to a fluid flow path, distal will typically refer to a downstream location in the fluid flow path, and proximal will typically refer to an upstream location, unless otherwise specifically noted. Anatomically, distal generally refers to "away from the heart" and proximal generally refers to "toward the heart."

A system for treating an aortic aneurysm according to the present invention typically includes a first prosthesis or precursor stent and at least one second prosthesis. In preferred embodiments of the invention, the components of the system are delivered intraluminally to the site of the aneurysm using a catheter or the like. One skilled in the art will therefore recognize that it is beneficial to deliver the components of the system in a closed or first position, and to deploy the component in its functional location by expanding the component into an open or second position.

Each of the components of the system will now be described in more detail. Any references to the Figures will be used to illustrate one or more exemplary embodiments of the invention, without intending to limit the invention thereby.

System

A system according to the present invention may include one or more prostheses. In the exemplary system shown in FIG. 1, the system includes a first prosthesis 10 and two second prostheses 11a and 11b, which, in combination, bypass an aneurysm 100. In preferred embodiments of the invention, a proximal portion of the system may be positioned in a portion 101 of an artery upstream of the aneurysm 100, and a distal portion of the system may be positioned in a downstream portion 102 of the artery or a different artery.

A prosthesis of the present invention includes a support, stent, or lattice of interconnected struts defining an interior space having an open proximal end and an open distal end. The lattice also defines an interior surface and an exterior surface. The interior and/or exterior surfaces of the lattice, or a portion of the lattice, may be covered by or support at least one covering material, such as a foam or graft material.

As noted in more detail below in relation to specific system components, some prostheses of the present invention may be configured to seal and/or anchor the system in place, and/or to receive and position other prostheses. Typically these prostheses do not themselves define a fluid flow path. Other prostheses may be configured to define at least one fluid flow path. Typically, these prostheses define a channel or the like through which fluid, such as blood, flows. This channel or fluid flow path typically begins upstream of, or in an upstream portion of, a component of the system. In some embodiments of the invention, the fluid flow path bypasses the aneurysm.

Figure 8:
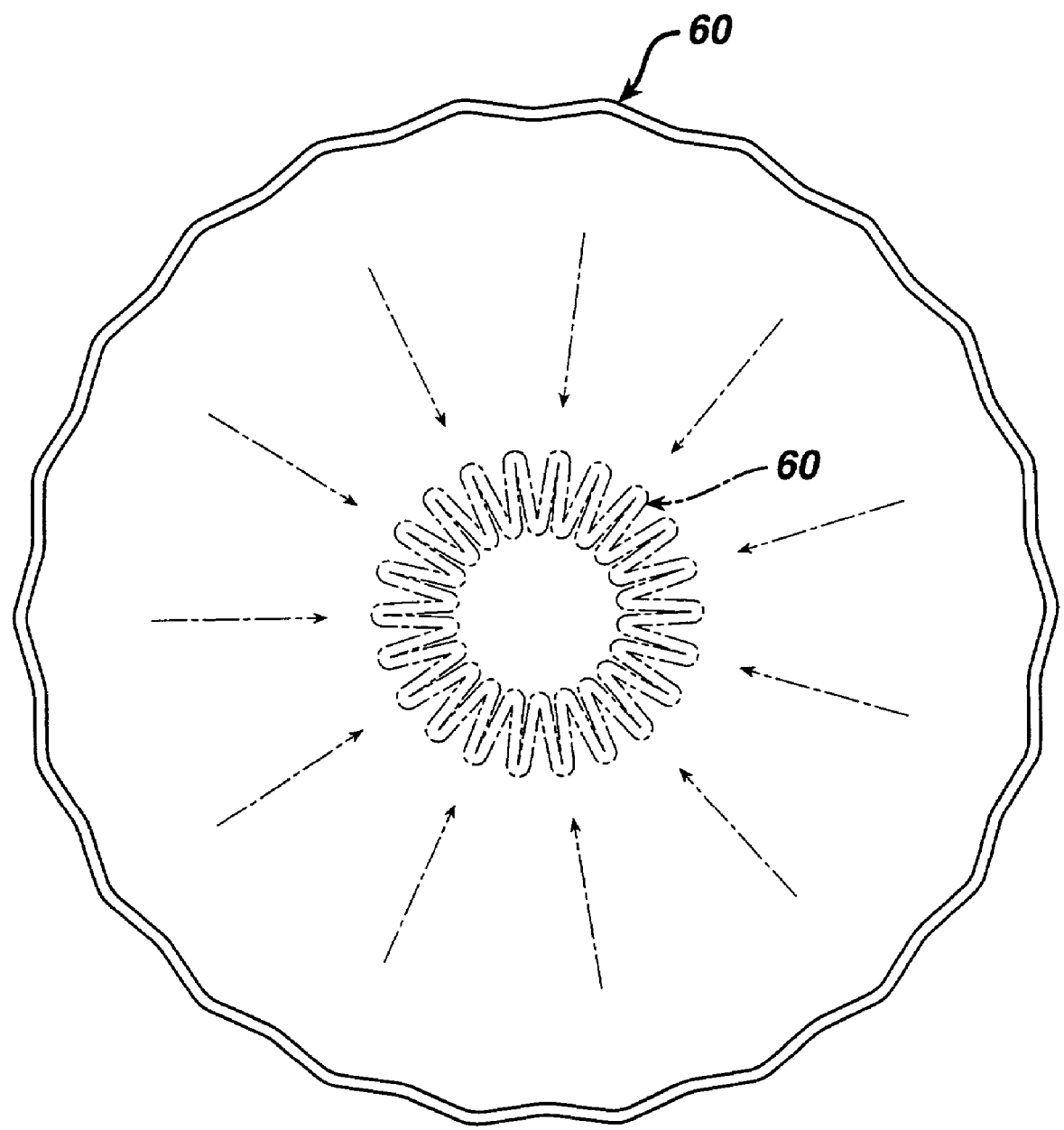
FIG. 8 is an end view of the graft material, taken along view line 8—8 shown in FIG. 6, illustrating the graft material in its unexpanded or crimped configuration, and in its fully expanded configuration.

In preferred embodiments of the invention, a prosthesis is moveable between an expanded or inflated position and an unexpanded or deflated position, and any position therebetween. An exemplary embodiment of this feature of the invention is shown in FIG. 8 and is intended to generally illustrate a stent or stent graft in its expanded or unexpanded position. In some exemplary embodiments of the invention, it may be desirable to provide a prosthesis that moves only from fully collapsed to fully expanded as indicated by the arrows in FIG. 8. In other exemplary embodiments of the invention, it may be desirable to expand the prosthesis, then collapse or partially collapse the prosthesis. Such capability is beneficial to the surgeon to properly position or re-position the prosthesis. In accordance with the invention, the prosthesis may be self-expanding, or may be expandable using an inflatable device, such as a balloon or the like.

An exemplary embodiment of a system for treating an abdominal aortic aneurysm according to the present invention is shown in FIG. 1. For the purpose of this embodiment, the system is deployed in the infrarenal neck 101 of the abdominal aorta, upstream of where the artery splits into right and left common iliac arteries. FIG. 1 shows first prosthesis or stent gasket 10 positioned in the infrarenal neck 101; two second prostheses, 11a and 11b, the proximal ends of which matingly engage a proximal portion of stent gasket 10, and the distal ends of which extend into a common iliac artery 1 or 2. As illustrated, the body of the prosthesis forms a conduit or fluid flow path that passes through the location of the aneurysm 100. In preferred embodiments of the invention, the components of the system define a fluid flow path that bypasses the section of the artery where the aneurysm is located. Above the first prosthesis are the renal arteries 3, 4.

These and other features of the prosthetic devices and systems of the present invention will be described in more detail below.

First Prosthesis or Sealing Prosthesis

The first prosthesis includes a support matrix or stent that supports a sealing material or foam, at least a portion of which is positioned across a biological fluid flow path, e.g., across a blood flow path. In preferred embodiments of the invention, the first prosthesis, the stent, and the sealing material are radially expandable, and define a hollow space between a proximal portion of the prosthesis and a distal portion of the prosthesis. The first prosthesis may also include one or more structures for positioning and anchoring the prosthesis in the artery, and one or more structures for engaging and fixing at least one second prosthesis in place, e.g., a bypass prosthesis.

The support matrix or stent of the first prosthesis may be formed from a wide variety of materials, may be configured in a wide variety of shapes, and their shapes and uses are well known in the art. Exemplary prior art stents are disclosed in U.S. Pat. No. 4,733,665 (Palmaz); U.S. Pat. No. 4,739,762 (Palmaz); and U.S. Pat. No. 4,776,337 (Palmaz), each of the foregoing patents being incorporated herein by reference.

In preferred embodiments of the invention, the stent of the first prosthesis is a collapsible, flexible, and self-expanding lattice or matrix formed from a metal or metal alloy, such as nitinol or stainless steel. Structures formed from stainless steel may be made self-expanding by configuring the stainless steel in a predetermined manner, for example, by twisting it into a braided configuration. More preferably, the stent is a tubular frame that supports a sealing material. The term tubular, as used herein, refers to any shape having a sidewall or sidewalls defining a hollow space or lumen extending therebetween; the cross-sectional shape may be generally cylindrical, elliptic, oval, rectangular, triangular, or any other shape. Furthermore, the shape may change or be deformable as a consequence of various forces that may press against the stent or prosthesis.

The sealing material or gasket member supported by the stent may be formed of a wide variety of materials, may be configured in a wide variety of shapes, and their shapes and uses are well known in the art. Exemplary materials for use with this aspect of the invention are disclosed in U.S. Pat. No. 4,739,762 (Palmaz) and U.S. Pat. No. 4,776,337 (Palmaz), both incorporated herein by reference.

The sealing material or gasket member may comprise any suitable material. Exemplary materials are composed of a biodurable and biocompatible material, including but are not limited to, open cell foam materials and closed cell foam materials. Exemplary materials include polyurethane, polyethylene, polytetrafluroethylene; and other various polymer materials, preferably woven or knitted, that provide a flexible structure, such as Dacron®. Highly compressible foams are particularly preferred, preferably to keep the crimped profile low for better delivery. The sealing material or foam is preferably substantially impervious to blood when in a compressed state.

The sealing material may cover one or more surfaces of the stent i.e., can be located along an interior or exterior wall, or both, and preferably extends across the proximal end or a proximal portion of the stent. The sealing material helps impede any blood trying to flow around the first prosthesis, e.g., between the first prosthesis and the arterial wall, and around one or more bypass prostheses after they have been deployed within the lumen of the first prosthesis (described in more detail below).

In preferred embodiments of the invention, the sealing material stretches or covers a portion of the proximal end of the stent and along at least a portion of the outside wall of the stent.

In some embodiments of the invention, it may be desirable for the portion of the sealing material covering the proximal portion of the stent to include one or more holes, apertures, points, slits, sleeves, flaps, weakened spots, guides, or the like for positioning a guidewire, for positioning a system component, such as a second prosthesis, and/or for engaging, preferably matingly engaging, one or more system components, such as a second prosthesis. For example, a sealing material configured as a cover or the like, and having a hole, may partially occlude the stent lumen.

These openings may be variously configured, primarily to conform to its use. These structures promote proper side by side placement of one or more, preferably multiple, prostheses within the first prosthesis, and, in some embodiments of the invention, the sealing material may be configured or adapted to assist in maintaining a certain shape of the fully deployed system or component. Further, these openings may exist prior to deployment of the prosthesis, or may be formed in the prosthesis as part of a deployment procedure. The various functions of the openings will be evident from the description below. In preferred embodiments of the invention, the sealing material is a foam cover that has a single hole.

The sealing material may be attached to the stent by any of a variety of connectors, including a plurality of conventional sutures of polyvinylidene fluoride, polypropylene, Dacron®, or any other suitable material and attached thereto. Other methods of attaching the sealing material to the stent include adhesives, ultrasonic welding, mechanical interference fit and staples.

One or more markers may be optionally disposed in or on the stent between the proximal end and the distal end. Preferably, two or more markers are sized and/or positioned to identify a location on the prosthesis, or to identify the position of the prosthesis, or a portion thereof, in relation to an anatomical feature or another system component.

First prosthesis is typically deployed in an arterial passageway upstream of an aneurysm, and functions to open and/or expand the artery, to properly position and anchor the various components of the system, and, in combination with other components, seal the system or portions thereof from fluid leaks. For example, the sealing prosthesis may be deployed within the infrarenal neck, between an abdominal aortic aneurysm and the renal arteries of a patient, to assist in repairing an abdominal aortic aneurysm.

Figure 2:
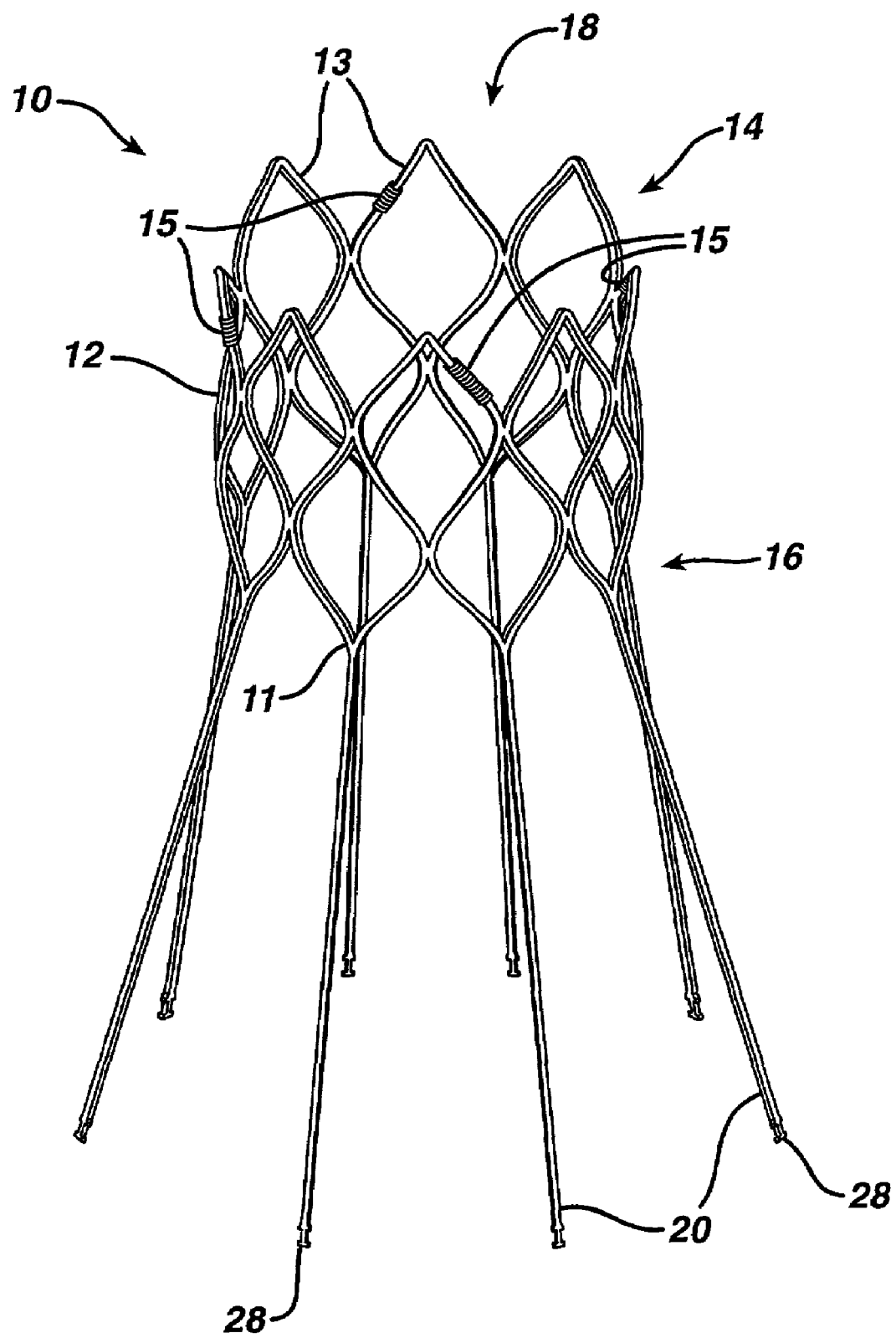
FIG. 2 is a perspective view of a stent for a first prosthesis, shown for clarity in an expanded state.
Figure 3:
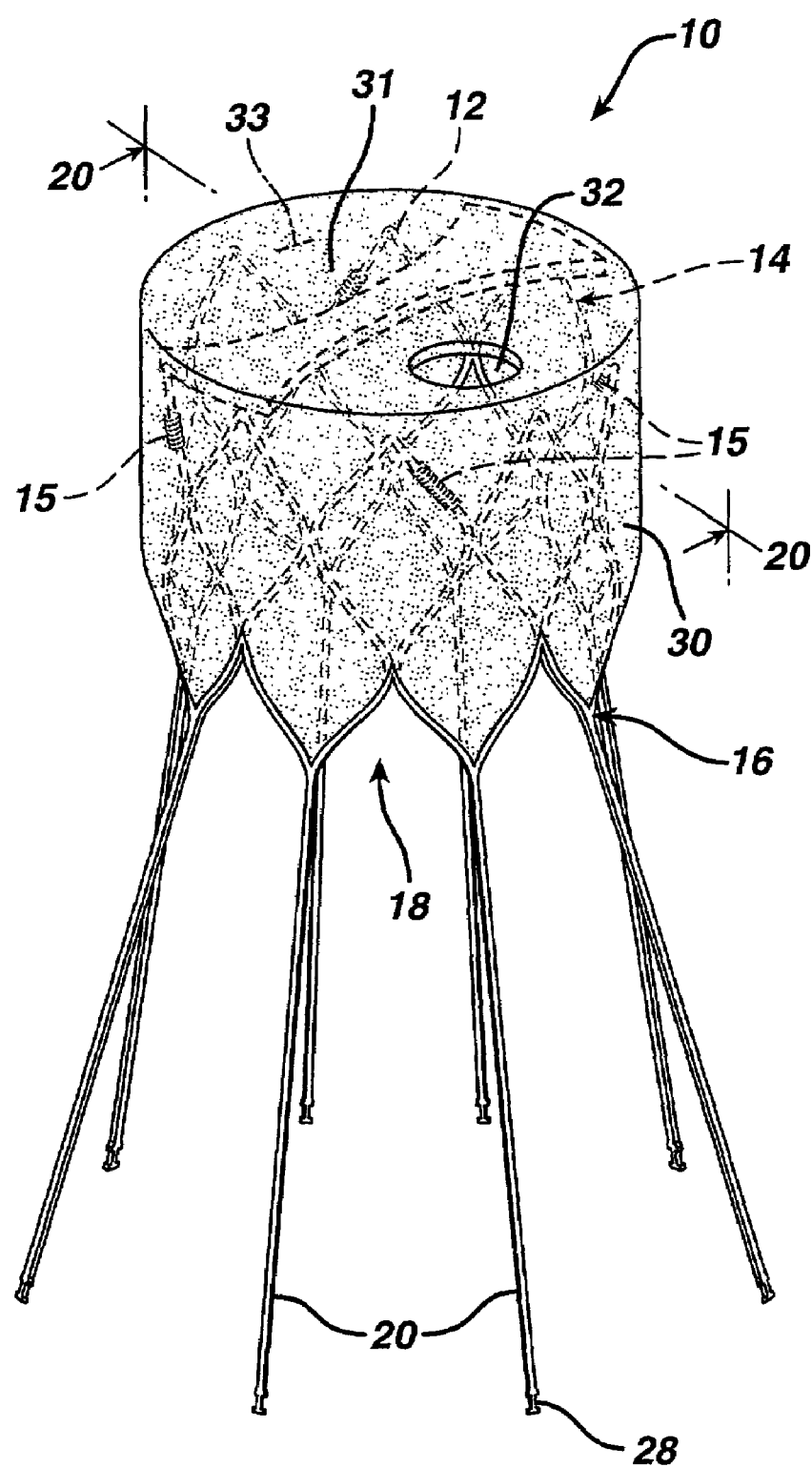
FIG. 3 is a perspective view of a first prosthesis having a stent covered by a graft material.

FIGS. 1–3 show an exemplary first prosthesis 10 of the present invention. First prosthesis 10 includes a cylindrical or oval self-expanding lattice, support, or stent 12, typically made from a plurality of interconnected struts 13. Stent 12 defines an interior space or lumen 18 having two open ends, a proximal end 14 and a distal end 16. One or more markers 15 may be optionally disposed in or on the stent between the proximal end 14 and the distal end 16.

Stent 12 may further include at least two, but preferably eight (as shown in FIG. 2) spaced apart longitudinal legs 20. Preferably, there is a leg extending from each apex 11 of diamond shaped interconnected struts 13. At least one leg 20, but preferably each leg 20, includes a flange 28 adjacent its distal end which, as is described in greater detail below, allows for the stent to be retrievable into its delivery apparatus after partial or nearly full deployment so that it can be turned, or otherwise repositioned for proper alignment.

FIG. 3 shows the sealing material 30 covering the proximal end of the stent gasket 10. In the embodiment shown in FIG. 3, sealing prosthesis 10 includes a gasket or sealing material 30 having a first opening or hole 32 and a second opening or slit 33. The gasket material 30 covers at least a portion of the interior or exterior of the stent, and most preferably covers substantially all of the exterior of the stent. For example, gasket material 30 may be configured to cover stent 12 from the proximal end 14 to the distal end 16, but preferably not covering longitudinal legs 20.

The sealing material helps impede any blood trying to flow around bypass prostheses 11a and 11b after they have been deployed (as shown in FIG. 1), and from flowing around the stent gasket 10 itself. For this exemplary embodiment, sealing material 30 is a compressible member or gasket located along the exterior of the stent 12 and at least a portion of the interior of the stent 12.

Figure 20:
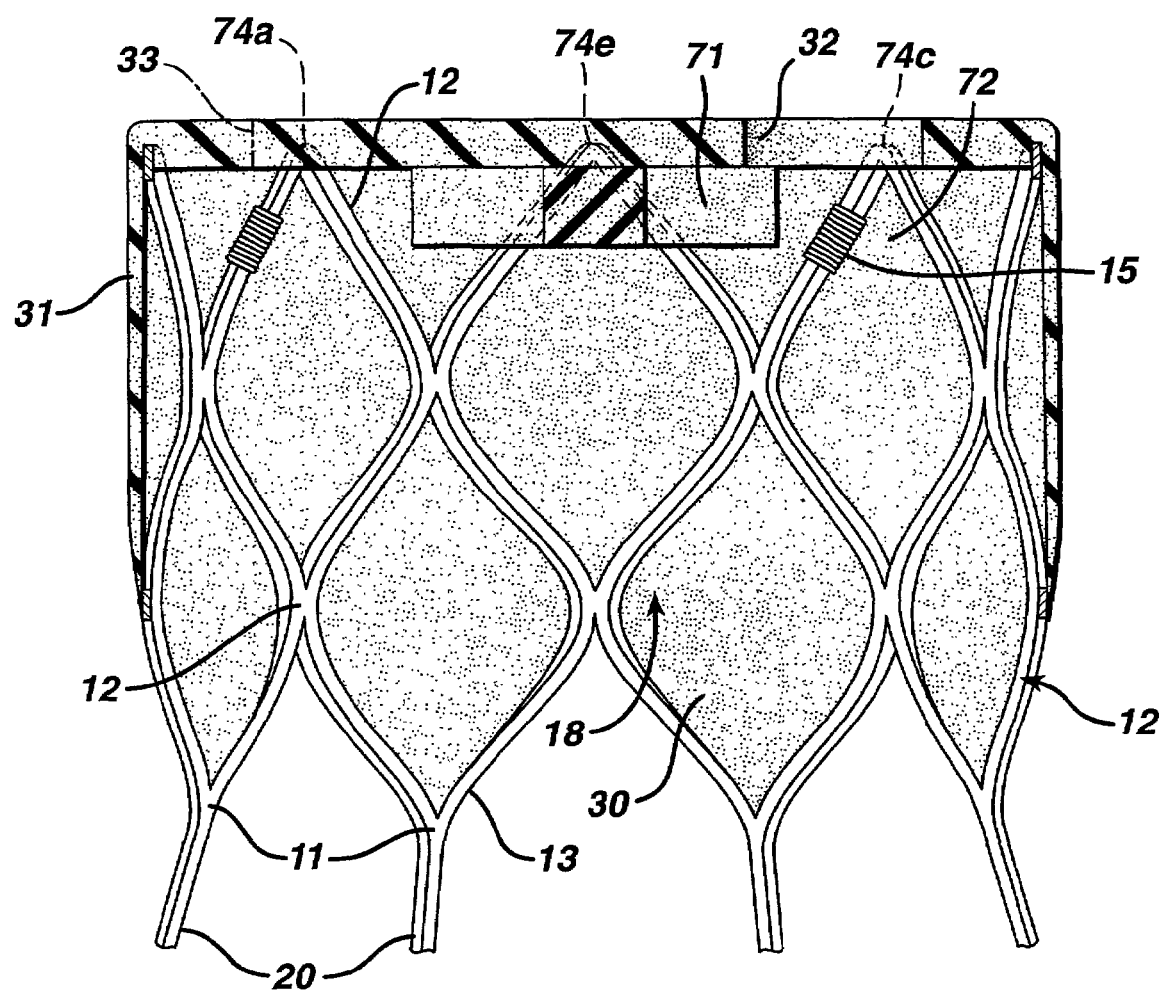
FIG. 20 is a side cross section of a first prosthesis taken along section line 20—20 shown in FIG. 3 according to the present invention.

Preferred embodiments of the invention are illustrated in FIGS. 20 and 21 (a–c). These figures show a first prosthesis 10 having a gasket material 30 that covers at least a portion of the proximal end of the first prosthesis 10. The gasket material 30 preferably includes a partition that extends approximately across the diameter of the cross section of the first prosthesis 10, wherein the partition includes a thicker gasket material, or further includes a foam or the like. The partition may be formed from any of the gasket or foam materials described above.

The exemplary embodiments illustrated in FIGS. 20 and 21 (a–c) include a thicker partition 71 in roughly an hourglass shape, although other shapes and sizes may be used. The partition defines at least one section 72 within the prosthesis having less material or the like, these sections being configured for receiving a proximal end of a second prosthesis, as is described in more detail below. In the exemplary embodiments shown in FIGS. 21 (a–c), partition 71 defines a first section 72a and a second section 72b; first section 72a is configured to receive a first second prosthesis 11a, and second section 72b is configured to receive a second second prosthesis 11b, as described below.

In accordance with the present invention, it may be desirable to include one or more fibers, threads, sutures, filaments, straps, or the like for further defining a section 72. In the description below, the word fiber will be used as a shorthand descriptor for the element that includes fibers, threads, filaments, straps, or the like. In preferred embodiments of the invention, the fiber, etc., assists in positioning a second prosthesis 11a, b.

In accordance with the present invention, the fiber or thread may be formed from any material and/or comprise any construction suitable for use in a biological environment, e.g., suitable for use in a blood vessel. The fiber may be woven or non-woven, formed of a synthetic or natural material, and/or single or multi-filament. Exemplary materials for forming the fiber or thread include but are not limited to polyester, Teflon®, polyurethane, silicone, polyethylene terepthalate, and expanded polytetrafluoroethylene (ePTFE). The fiber or thread may also take on other forms. For example, the fiber or thread may be formed from glues or adhesives, or by melting sections of the gasket material. In addition, the fiber or thread may comprise struts deformed out of the circumferential plane.

The end or ends of the fiber may be unattached or attached. In a preferred embodiment of the invention, both ends of the fiber are attached or fixed. For example, the ends may be sewn or fixed to the cover 31. In a preferred embodiment of the invention, the ends of the fiber are fixed to a strut 13, even more preferably to a proximal portion of stent 12. One or more portions of the fiber may be fixed to the stent 12 or the strut 13 by threading, knotting, sewing, with adhesives, or any other mechanism for fixing the portion of the fiber in place.

Figure 21A:
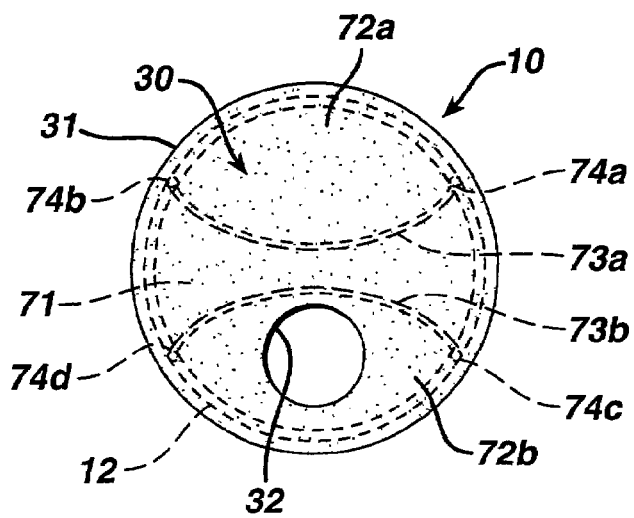
FIGS. 21 (a–c) are top views of alternate embodiments of a cover on a first prosthesis according to the present invention.
Figure 21B:
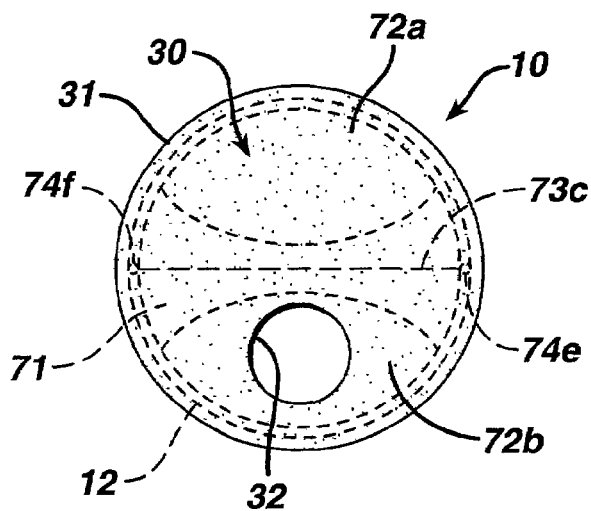
Figure 21C:
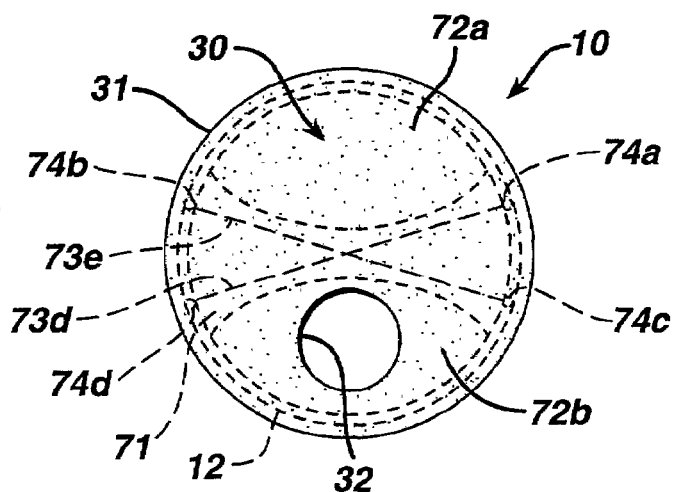

In the exemplary embodiments of the invention illustrated in FIGS. 21 (a–c), the fiber may be variously configured. In FIG. 21a, fibers 73a and 73b may be interwoven in the cover 31, and define or form first section 72a and a second section 72b, as noted above. As shown, the ends of the fibers may be fixed to a strut; see 74a, 74b, 74c, and 74d. In FIG. 21b, a single fiber 73c may be positioned across the diameter of the cover 31, and fixed to a strut at 74e and 74f. In FIG. 21c, one or more crossed fibers 73d and 73e may be used to form or define sections 72a and 72b respectively. In the illustrated embodiments, the ends may be attached to the stent 12 at 74a, 74b, 74c, and 74d.

In some embodiments according to the present invention, it may be desirable to use a fiber that is frangible or breakable. In these exemplary embodiments of the invention, the fiber breaks as the unexpanded prosthesis is expanded to its fully deployed position. Alternately, the ends of the fibers may be releasably fixed to the stent or strut when the prosthesis is in a collapsed condition, with one or more ends releasing as the prosthesis expands to its fully deployed position.

These structures promote proper side by side placement of one or more, preferably multiple, prostheses within the first prosthesis 10.

Second Prosthesis

The second prosthesis is a bypass conduit or the like that is typically deployed in an arterial passageway upstream of an aneurysm, and establishes a fluid flow path through the system or a portion thereof. In some embodiments of the invention, the second prosthesis defines a fluid flow path that passes through the arterial segment having the aneurysm, e.g., bypassing the aneurysm. In these exemplary embodiments of the invention, the second prosthesis extends from a healthy portion of the artery, through the arterial segment having the aneurysm, and into another healthy portion of the artery or another artery. The second prosthesis functions to bypass the portion of the conduit containing the aneurysm, and to properly position and/or anchor the proximal end of the system in an artery. In some embodiments of the invention, the second prosthesis defines a fluid flow path from one portion of the system, e.g., a proximal portion or end, to another portion, e.g., a distal portion or end, or an intermediate portion.

The second prosthesis may also include one or more structures for positioning and anchoring the second prosthesis in the artery or in the first prosthesis. In a preferred embodiment of the invention, the second prosthesis is adapted to engage the first prosthesis.

One or more markers may be optionally disposed in or on the stent between the proximal end and the distal end. Preferably, two or more markers are sized and/or positioned to identify a location on the prosthesis, or to identify the position of the prosthesis, or a portion thereof, in relation to an anatomical feature or another system component. In preferred embodiments of the invention, fluoroscopically identifiable sutures or staples are used; these sutures or staples may also attach the graft material to the stent.

FIGS. 1 and 4–6 show an exemplary second or bypass prosthesis 11a, b of the present invention. Second prosthesis 11a, b includes a substantially cylindrical self-expanding lattice, support, or stent 40, typically made from a plurality of interconnected struts 44. Lattice 40 defines an interior space having two open ends, a proximal end 41 and a distal end 42. The interior and/or exterior surfaces of lattice 40 may be covered by or support at least one graft material 60.

The second prosthesis typically includes a support matrix or stent that supports a graft material. One end of the second prosthesis is typically adapted to engage one or more portions of the first prosthesis. In preferred embodiments of the invention, the proximal end of second prosthesis is adapted to matingly engage a proximal portion of first prosthesis. The second prosthesis may optionally include at least one attachment structure on its distal end for engaging and securing the prosthesis in a portion of an artery downstream of the aneurysm. These and other features of the second prosthesis will be described in more detail below.

Extension Prosthesis

An extension prosthesis according to the present invention is a conduit or the like that is typically deployed in an arterial passageway, and extends from a second or bypass prosthesis into another portion of the artery, another artery, or a portion of a bifurcated arterial network. The system comprising the extension prosthesis functions to bypass the portion of the conduit containing the aneurysm, and to properly position and/or anchor the proximal end of the system in an artery. The extension prosthesis may also include one or more structures for positioning and anchoring the extension prosthesis in the artery or in the second prosthesis. In a preferred embodiment of the invention, the extension prosthesis is adapted to engage a distal portion of the second prosthesis.

Figure 16A:
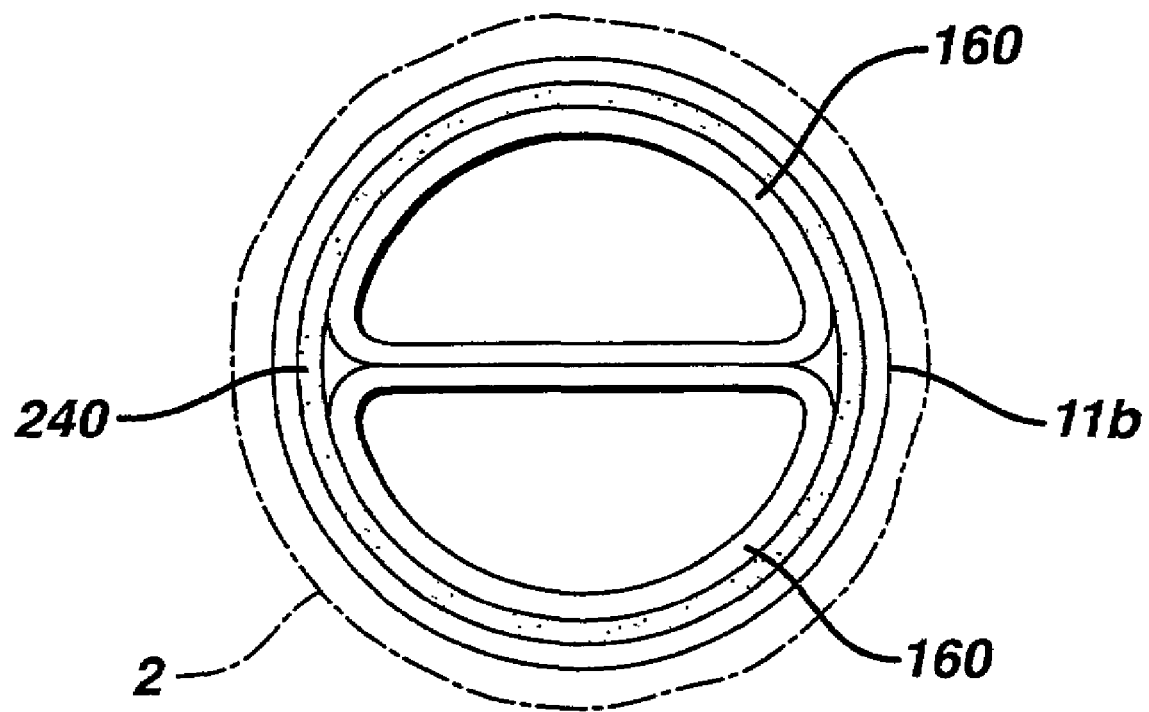
FIG. 16a is a cross-sectional view of the first and second extension prosthesis taken along section line 16a—16a, shown in FIG. 16.

FIG. 16 shows an exemplary extension prosthesis 160 of the present invention. In exemplary embodiments of the invention, extension prosthesis 160 may be configured as described above for second prosthesis 11a or 11b (FIGS. 4–6). Extension prosthesis 160 includes a substantially cylindrical self-expanding lattice, support, or stent, typically made from a plurality of interconnected struts. Stent defines an interior space having two open ends, a proximal end and a distal end. The interior and/or exterior surfaces of the stent may be covered by or support at least one graft material.

The extension prosthesis 160 typically includes a support matrix or stent that supports a graft material. One end of the extension prosthesis is typically adapted to engage one or more portions of second prosthesis 11a, b. In preferred embodiments of the invention, the distal end of second prosthesis 11a, b is adapted to matingly engage a proximal portion 161 of extension prosthesis 160. In preferred embodiments of the invention, the engagement between the second prosthesis and the extension prosthesis is fluid tight, specifically blood-tight. One skilled in the art will recognize that there are a variety of configurations and structures on one or both of the second prosthesis or the extension prosthesis that may provide mechanical resistance to separation at the junction between the two prostheses. Such alternative configurations and structures are included within the present invention.

In adapting the extension prosthesis to engage the second prosthesis, the proximal end of the extension prosthesis may be flared or unflared. In an exemplary embodiment of the invention, the proximal end of extension prosthesis 160 may be slightly outwardly flared, preferably to more easily effect the mating engagement between the second prosthesis and the extension prosthesis. It is intended that the length of the flared portion of the extension prosthesis should approximate the length of overlap between the distal end of the second prosthesis and the proximal end of the extension prosthesis.

The extension prosthesis may also optionally include at least one attachment structure on its distal portion 162 for engaging and securing the prosthesis in a portion of an artery downstream of the aneurysm. These and other features of the extension prosthesis will be described in more detail below.

In accordance with the present invention, the communication between the bypass or second prosthesis and the extension prosthesis or prostheses may include one or more elements that in combination effect a fluid tight seal. As noted above, the fluid tight seal may be achieved by sealingly affixing an extension receptacle 240 (FIG. 16a) across the interior of a distal portion of the bypass or second prosthesis. In one exemplary embodiment of the invention, the extension receptacle 240 fully occludes the fluid flow path through the bypass prosthesis. In this exemplary embodiment of the invention, the extension receptacle 240 may be punctured or opened in a centrally located portion in order to engage or receive the extension prosthesis.

In another exemplary embodiment of the invention, the extension receptacle 240 may include one of more apertures configured to receive an extension prosthesis.

In accordance with the present invention, the extension receptacle 240 may be formed from a gasket material, preferably a compressible gasket material. The gasket material may comprise any suitable material. The gasket material may be formed from any number of materials known to those of ordinary skill in the art including open cell foam materials and closed cell foam materials. Exemplary materials include polyurethane, polyethylene, polytetrafluroethylene, other various polymer materials which are woven or knitted to provide a flexible structure such as Dacron®. Highly compressible foams are particularly preferred, so as to keep the crimped profile low for better delivery. The gasket material for the extension receptacle 240 may be attached in any number of suitable ways. As illustrated in FIG. 3, the gasket 30 for the first prosthesis may be attached to expandable member 12 by any number of means including a plurality of conventional sutures of polyvinylidene fluoride, polypropylene, Dacron®, or any other suitable material and attached thereto. Other methods of attaching gasket 30 to an expandable member or stent include adhesives, ultrasonic welding, mechanical interference fit and staples, or a combination of these methods. Any of these methods may be utilized with the extension receptacle 240.

As is apparent to one skilled in the art, it may be desirable for the system and/or one or more prostheses described above to achieve as large a fluid flow path as possible, within the confines of an artery. As noted above, the size of the fluid flow path is in part defined by the size of the lumen of a stent or prosthesis. It has been determined that the lowest functional diameter of a prosthesis or stent should be greater than about 6 mm, preferably about 12 mm.

Figure 18:
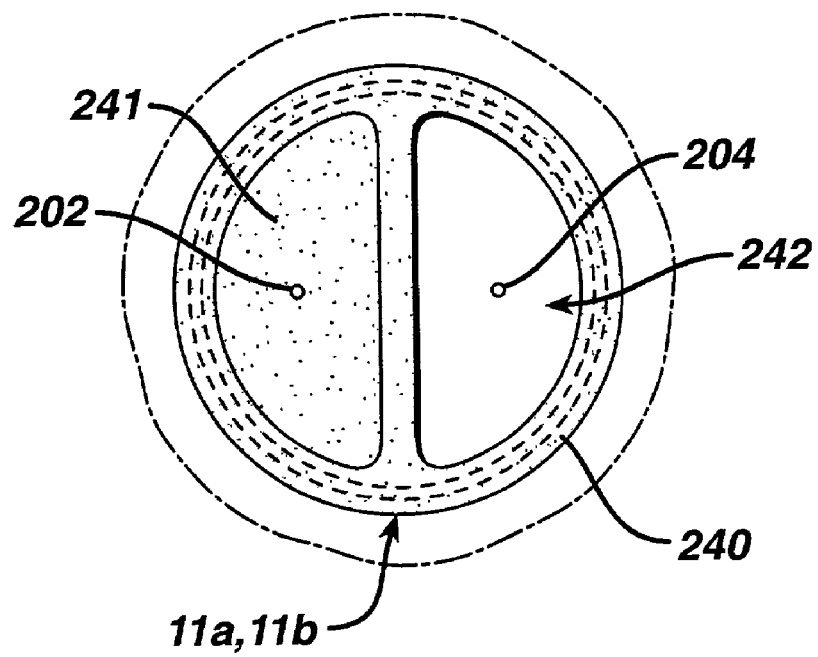
FIG. 18 is a end view of an extension receptacle configured as a cover for the distal end of a bypass prosthesis.
Figure 19:
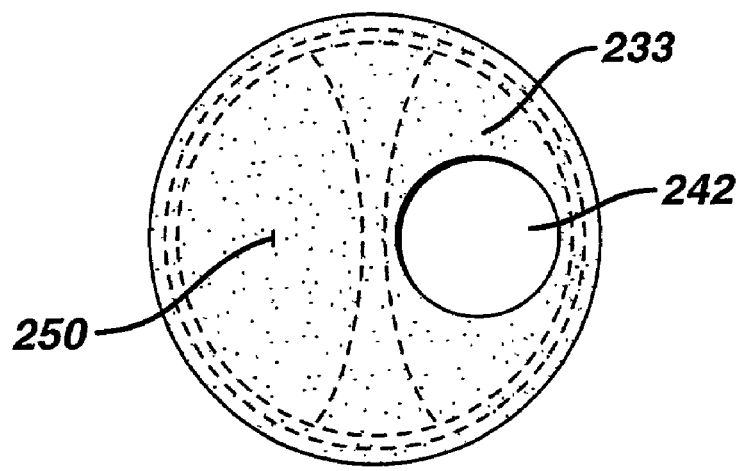
FIG. 19 is a end view of an extension receptacle configured as an occlusion member configured to engage an internal and distal portion of a bypass prosthesis.

As seen from FIGS. 18 and 19, an exemplary extension receptacle 240 may comprise an occlusive member 241 attached to a distal portion of the bypass or second prosthesis 11a, b. The occlusive member 241 may cover a predetermined portion of the interior of the bypass prosthesis. The extension receptacle 240 covers the interior of the bypass prosthesis in such a way that a lumen 242 of the extension receptacle provides access between the proximal and distal ends of the bypass prosthesis. In one exemplary embodiment, the cover blocks about one half of the lumen as taken from a cross section of the bypass prosthesis perpendicular to its longitudinal axis. Occlusive member 241 further includes an opening extending therethrough so as to receive a guidewire 202 for guiding one or more prostheses to a target site. Thereafter, when a second guidewire 204 for a second prosthesis is introduced, the occlusive member 241 will prevent it from going through the same opening as guidewire 202 is positioned, and will force it to go through the other half of the interior of the extension receptacle 240. This helps to ensure proper side by side placement of the two prostheses.

Another exemplary embodiment of the extension receptacle of the present invention is shown in FIG. 19. In this exemplary embodiment, the extension receptacle is a gasket or the like configured to engage or cover the distal end of the bypass or second prosthesis, the extension receptacle comprising an integral gasket member and occlusive member 233. Occlusive member 233 is much like a drum which stretches across the top of the stent and along its sides. Occlusive member 233 has a small opening or slit 250 to accommodate the initial guidewire that it is deployed with, and a larger opening 242 for insertion of the second guidewire after the prosthesis has been deployed.

Stent

Any of the stents of the present invention may form a support or lattice structure suitable for supporting a graft material. In preferred embodiments of the invention, the stent defines a channel through which a fluid, such as blood, may flow. A typical stent comprises an expandable lattice or network of interconnected struts. In preferred embodiments of the invention, the lattice is machined from an integral tube of material.

In accordance with the present invention, the stent may be variously configured. For example, the stent may be configured with struts or the like that form repeating geometric shapes. One skilled in the art will readily recognize that a stent may be configured or adapted to include certain features and/or to perform a certain function(s), and that alternate designs may be used to promote that feature or function.

In some exemplary embodiments of the invention, the struts of the stent gasket form a matrix having diamond shapes. In the exemplary embodiment of the invention shown in FIG. 2, the matrix or struts of stent 10 is configured into diamond shapes, preferably having approximately eight diamonds. In this exemplary embodiment of the invention, the fully expanded diamond pattern of a first prosthesis has angles of forty-five to fifty-five degrees at their distal and proximal ends.

Figure 5:
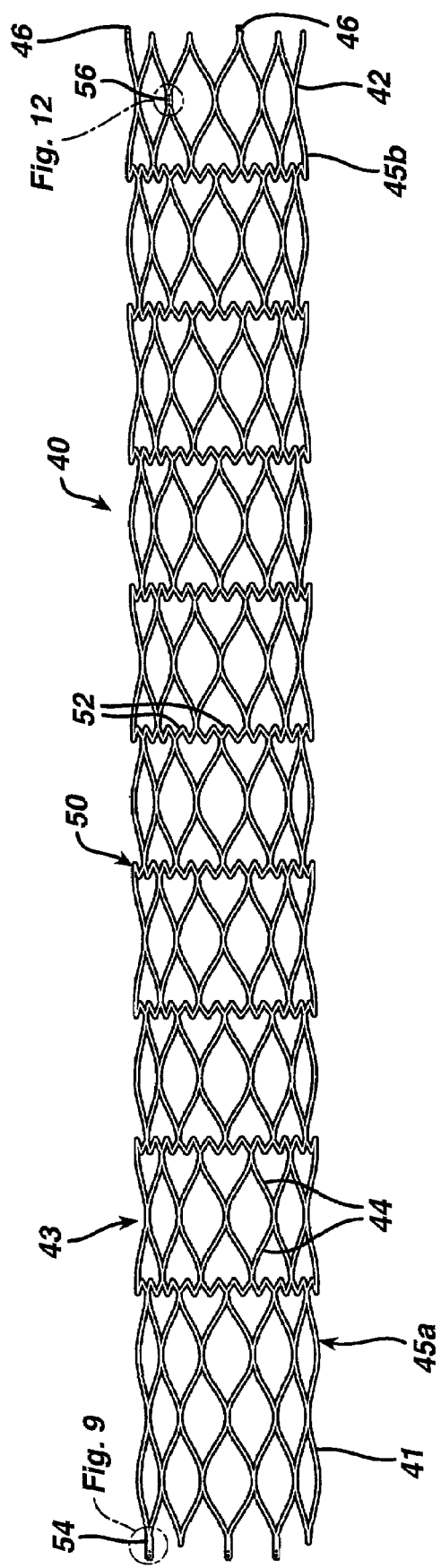
FIG. 5 is a side elevation of an stent for a second prosthesis, shown for clarity in an expanded state.

In the exemplary embodiment of the invention shown in FIG. 5, the matrix or struts of stent 40 may be configured into at least two hoops 43, each hoop 43 comprising a number of struts 44 having a diamond shape, having approximately nine diamonds. A second prosthesis, such as second prosthesis 40, may further include a zigzag shaped ring 50 for connecting adjacent hoops to one another. The zigzag shaped rings may be formed from a number of alternating struts 52, wherein each ring has fifty-four struts.

The diamond pattern for the anchors, as well as the other hoops, provide the hoops with radial and longitudinal stiffness. The longitudinal strength provides for better mechanical fixation of stent 40 to a graft material (described below). The radial strength provides the proximal hoop 45*a* with better attachment and sealing to the gasket material, and provides the distal hoop 45*b* with better fixation and sealing to the arterial wall. Further, the distal hoop may be flared, and may be exposed after the graft material has been attached to the stent.

In one preferred exemplary embodiment, the proximal and distal hoops have greater radial and longitudinal strength than the hoops therebetween. This creates a stent graft having stiff ends for anchoring, but a more flexible body for navigation through the vasculature. The stiffer ends may be accomplished by changing the dimensions of the struts for the end hoops, or by varying the heat treatment of the end hoops during manufacture. The rings allow the stent to bend more easily, and generally provide for more flexibility when the stent is being delivered through a tortuous vessel. When a non-compliant graft is attached to a stent, the strength of the diamond hoops scaffolds any graft folding into the blood flow lumen, while maintaining a tight kink radius.

In accordance with some embodiments of the present invention, the proximal and/or distal end of a stent may include one or more anchors and/or one or more struts of the stent configured into an anchor. One or more anchors, commonly referred to as recapture legs, may also be configured to releasably engage a delivery device, such as a catheter, or a portion thereof.

Figure 15:
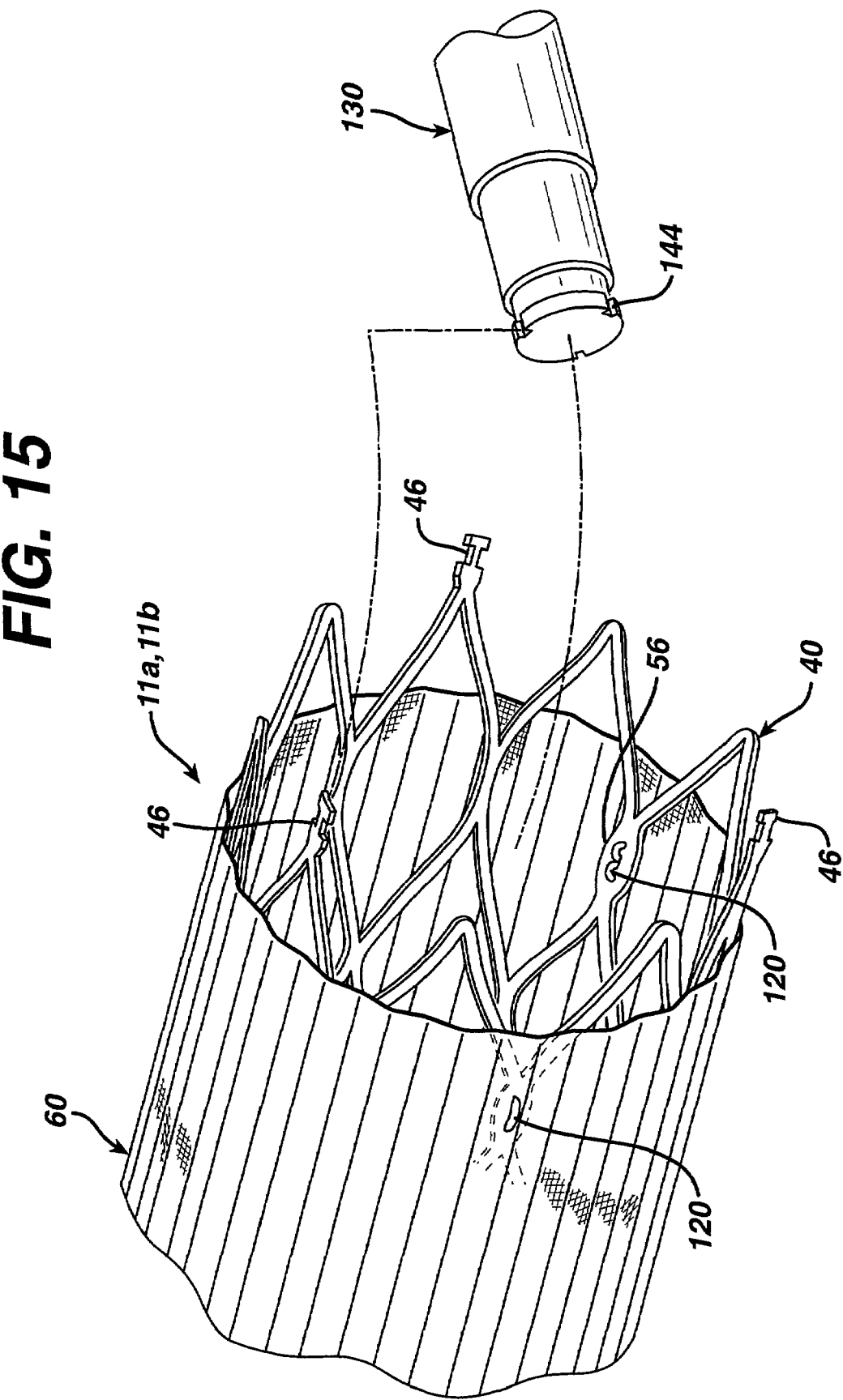
FIG. 15 is a partial, exploded perspective view of the proximal end of a second prosthesis of the present invention illustrating an anchoring and delivery system according to the invention.

The distal end of the stent is preferably configured to engage a complementary structure on a delivery device, such as a catheter or a portion thereof. For example, the distal end of the stent may include one or more keys that engage, preferably releasably engage, a corresponding latch on the catheter. An exemplary configuration is shown in FIG. 15. It is intended that the invention should not be limited by the precise structures used to engage the stent to the delivery device.

In the exemplary embodiments of the invention shown in FIGS. 1–3 and 15, the stent may include one or more anchors 28, 46 configured to engage a corresponding structure on a delivery device 130. In accordance with the present invention, the delivery apparatus may include a collar having one or more grooves or the like adapted to releasably engage one or more complementary structures on a stent or prosthesis of the present invention. For example, the delivery apparatus shown in FIG. 7 includes eight grooves 144 to configure the delivery device to releasably engage both the first prosthesis 10 in FIG. 1 (having eight anchors 28 as illustrated in FIG. 2), and the delivery apparatus shown in FIG. 15 includes three grooves 144 to configure the delivery device to releasably engage the second prosthesis 11*a, b* in FIG. 15 (having three anchors 46). Such an anchor/delivery device configuration is particularly suited to partially deploying a prosthesis of the present invention, and to position or re-position the prosthesis.

Any of the stents of the present invention may be formed of any material suitable for functioning in vivo as a support for graft material. A stent of the present invention may be formed of a wide variety of materials, all of which are well known to those skilled in the art. In some exemplary embodiments of the invention, the stent is formed from a metal or metal alloy. In preferred embodiments of the invention, the stent is formed from superelastic Nickel Titanium alloys (Nitinol). Descriptions of medical devices which use such alloys can be found in U.S. Pat. No. 4,665,906 and European Patent Application EP 0928606, both of which are hereby incorporated herein by reference. A stent according to the present invention is preferably laser cut from a tubular piece of nitinol and thereafter treated so as to exhibit shaped memory properties at body temperature. In preferred embodiments of the invention, the stent material is expandable or collapsible, i.e., moveable from a first closed position to a second open position, or vice versa.

Graft Material

An inner or outer surface of a stent of the present invention may be covered by or support a graft material.

Graft material 60 (FIGS. 4, 6, 8, 10, 11, 13, 14 and 15) can be made from any number of materials known to those skilled in the art, including woven polyester, Dacron®, Teflon®, polyurethane, porous polyurethane, silicone, polyethylene terephthlate, expanded polytetrafluoroethylene (ePTFE) and blends of various materials.

In some embodiments of the invention, it may be desirable to incorporate a biodegradable, or degradable material, such as albumin, collagen, or any type of collagen. A graft material that is biodegradable would erode or dissolve over time; it is believed that the eroding graft material may be replaced by one or more biofusion constituents.

The graft material may be variously configured, preferably to achieve predetermined mechanical properties. For example, the graft material may incorporate a single or multiple weaving and/or pleating patterns, or may be pleated or unpleated. For example, the graft may be configured into a plain weave, a satin weave, include continuous longitudinal pleats, interrupted pleats, annular or helical pleats, radially oriented pleats, or combinations thereof. Alternately, the graft material may be knitted or braided. In the exemplary embodiments of the invention in which the graft material is pleated, the pleats may be continuous or discontinuous. Also, the pleats may be oriented longitudinally, circumferentially, or combinations thereof.

Figure 6:
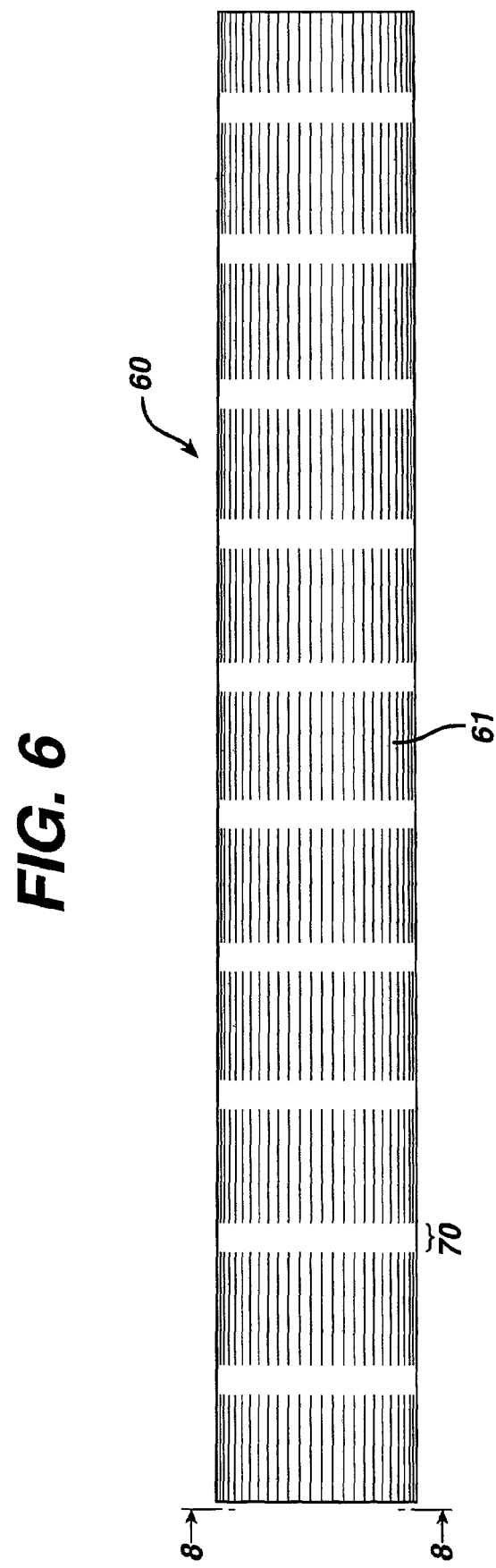
FIG. 6 is a side elevation of a longitudinally pleated graft material configured for placement on the stent of FIG. 5.

As shown in FIG. 6, graft material 60 may include a plurality of longitudinal pleats 61 extending along its surface, generally parallel to the longitudinal axis of the prosthesis. As shown in FIG. 8, the pleats allow the prosthesis to collapse around its center, much as it would be when it is delivered into a patient. As illustrated, the pleats come together as a series of radially oriented regular folds that pack together efficiently. This provides a relatively low profile delivery system, and provides for a controlled and consistent deployment therefrom. It is believed that this configuration minimizes wrinkling and other geometric irregularities. Upon subsequent expansion, the prosthesis assumes its natural cylindrical shape, and the pleats or folds uniformly and symmetrically open.

In addition, pleats 61 help facilitate stent graft manufacture, in that they indicate the direction parallel to the longitudinal axis, allowing stent to graft attachment along these lines, and thereby inhibiting accidental twisting of the graft relative to the stent after attachment. The force required to push the stent-graft out of the delivery system may also be reduced, in that only the pleated edges of the graft make frictional contact with the inner surface of the delivery system. One further advantage of the pleats is that blood tends to coagulate generally uniformly in the troughs of the pleats, discouraging asymmetric or large clot formation on the graft surface, thereby reducing embolus risk.

As shown in FIG. 6, the graft material may also include one or more, and preferably a plurality of, radially oriented pleat interruptions 70. The pleat interruptions are typically substantially circular and are oriented perpendicular to longitudinal axis. Pleat interruptions 70 allow the graft and prosthesis to bend better at selective points. This design provides for a graft material that has good crimpability and improved kink resistance.

The graft material as described above is preferably highly compressible, which also promotes a low crimped profile for better delivery characteristics.

In accordance with the present invention, the graft material may be impervious or substantially impervious to the flow of blood, or may be porous. A graft material is impervious if it prevents blood from passing through the graft material on contact with blood or after the graft material is saturated with blood. Choice of the flow characteristics of a graft material are well known to those skilled in the art, and are tied in part to the intended function of the prosthesis or portion of the prosthesis. For example, it may be desirable for the graft material that forms the cover of the first prosthesis to be impervious or substantially impervious to the flow of blood. Alternatively, it may be desirable for a graft material to be porous or partially porous to promote biofusion.

In addition, it is preferable that the gasket member be substantially impervious to the flow of blood, at least when in a partially compressed state. When used throughout for the present invention, materials which are substantially impervious to the flow of blood include materials which become substantially impervious to the flow of blood after being saturated with blood.

A graft material may be attached to a stent or to another graft material by any number of structures or methods known to those skilled in the art, including adhesives, such as polyurethane glue; a plurality of conventional sutures of polyvinylidene fluoride, polypropylene, Dacron®, or any other suitable material; ultrasonic welding; mechanical interference fit; and staples.

Figure 4:
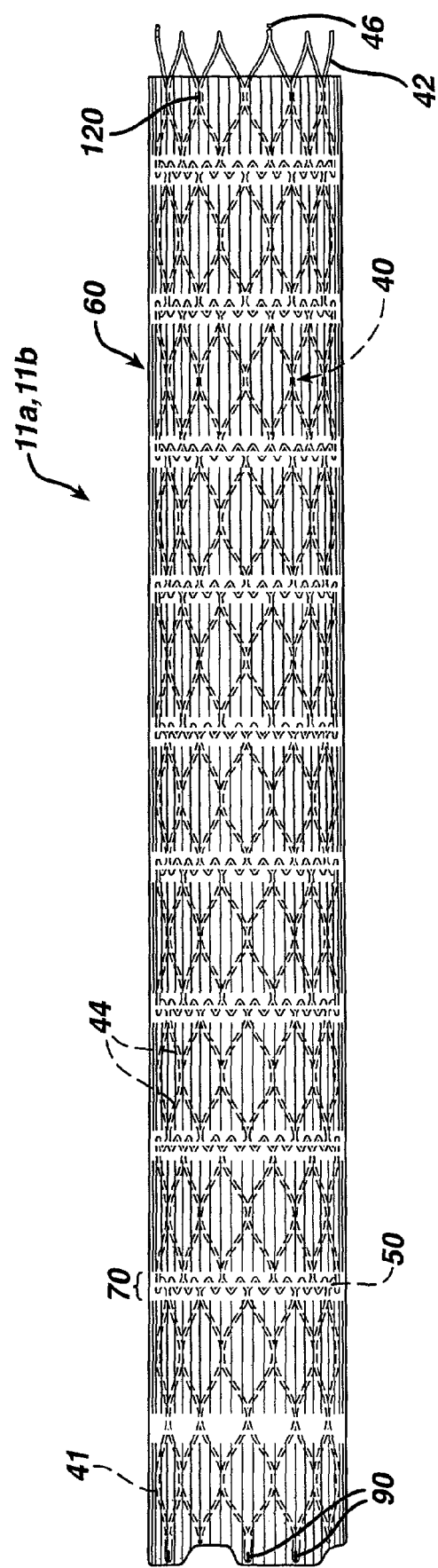
FIG. 4 is a side elevation of a second prosthesis having a stent covered by a graft material.

As stated above, a stent preferably has a graft member attached thereto. The graft member covers at least a portion of the interior or exterior of the stent, and most preferably covers substantially all of the exterior of the stent. In some exemplary embodiments of the invention, prosthesis 11a, b includes graft material 60 that covers only a portion of the distal end 42 of matrix 40 (FIG. 4).

In an alternate design, graft material may not be utilized on either end of the stent. For example, on any endolegs, prostheses, extension cuffs, stent gaskets or other covered stents, both ends thereof may be left uncovered. The body has the ability to cover the exposed portions of the stent with endothelial cells and thus these exposed portions become endothelialized or incorporated into the vessel wall. This may be an important factor in the long-term stability of the system. Essentially, over long periods of time, the aneurysmal sac can and will shrink if it is totally excluded from blood flow. This shrinkage changes the morphology of the aortic region that has been treated with the bypass prosthesis. If all ends of the system are firmly anchored in the actual vessel, as is the case when the ends are covered with endothelium cells, the system will be better able to withstand these morphological changes.

In accordance with the present invention, it may be highly desirable to provide a graft material that limits or substantially eliminates the amount of blood that passes between the graft and the arterial wall, to provide a catheter-delivered graft or prosthesis that extends through a longer portion of an artery, to improving the anchoring mechanisms between two prostheses, to improving the anchoring mechanism between the prosthesis and the arterial wall or an interluminal cavity within an artery, and to improve the fluid dynamic and performance characteristics of the implanted prosthesis.

Marker

As noted above, a stent and/or prosthesis of the present invention may include one or more markers. One skilled in the art will recognize that one or markers may be positioned on the stent, the graft material, or on the prosthesis. In preferred embodiments of the invention, the markers are used to identify the position of the stent or prosthesis in relation to a body part and/or in relation to another stent or prosthesis, and/or to identify the position of one part of the prosthesis relative to another part. In most preferred embodiments of the invention, the marker(s) is used to identify a position in vivo.

As shown in FIGS. 2 and 3, a stent, such as stent 12, preferably includes one or more radiopaque markers 15. Exemplary materials for forming markers include but are not limited to tantalum, platinum, iridium, and gold. As shown, markers 15 are coils of radiopaque metal, wrapped around the struts of the stent. Markers 15 are preferably made from 0.0075 inch diameter tantalum (Ta) wire wrapped tightly around the struts.

The number, location, and size of the markers may vary, and the markers may be used alone or in combination to identify the position of a particular portion of the prosthesis. For example, a proximal marker adjacent aperture 32 may be about 5 mm long and the proximal marker adjacent hole 33 may be about 2 mm long. Also, two distal markers may be one hundred eighty degrees apart, and a proximal marker may be positioned equidistant from each of the distal markers. In this exemplary configuration, the proximal marker then aids proper rotational positioning of the device.

Connectors

Some exemplary embodiments of a prosthesis according to the present invention may include one or more connectors. In some exemplary embodiments of the invention, the connectors are used to engage or connect one prosthesis or component to another. In some exemplary embodiments of the invention, the connectors may be used to attach the gasket material or graft material to a stent or lattice.

As noted above, one skilled in the art will recognize that a variety of materials and methodologies may be used to connect one prosthesis to another, or to attach the graft material to a stent. Exemplary connectors include but are not limited to sutures, staples, rivets, or the like. In preferred embodiments of the invention, the connector is a suture or staple, even more preferably, having a knotted or nub end. Further, a connector may be formed from a radiopaque material or a fluorescent material, each of which allow the connector to be used as a marker.

In accordance with the present invention, it may be desirable to incorporate in a prosthesis a connector adapted for use with a lattice-like stent. A first connector 54, an exemplary embodiment of which is shown in FIGS. 5 and 9–11, may be configured for use at an end portion of a stent, preferably at an end portion of a strut 44. A second connector 56, an exemplary embodiment of which is shown in FIGS. 5 and 12–14, may be configured for use at an internal portion of a stent, preferably at the junction between two struts 44.

Figure 9:
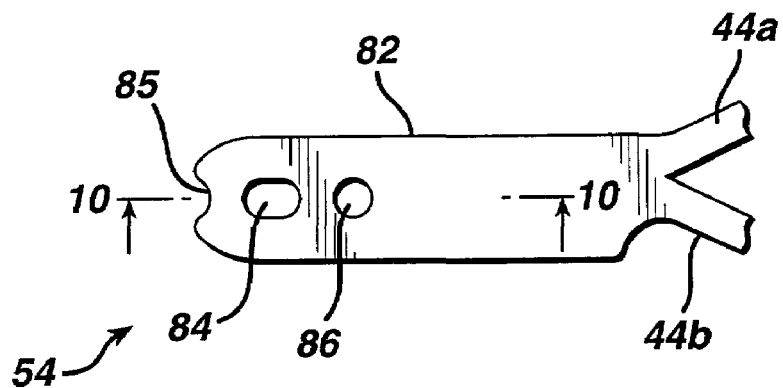
FIGS. 9 through 11 show an exemplary connector assembly of the present invention intended for use on an end portion of a stent or prosthesis.
Figure 10:
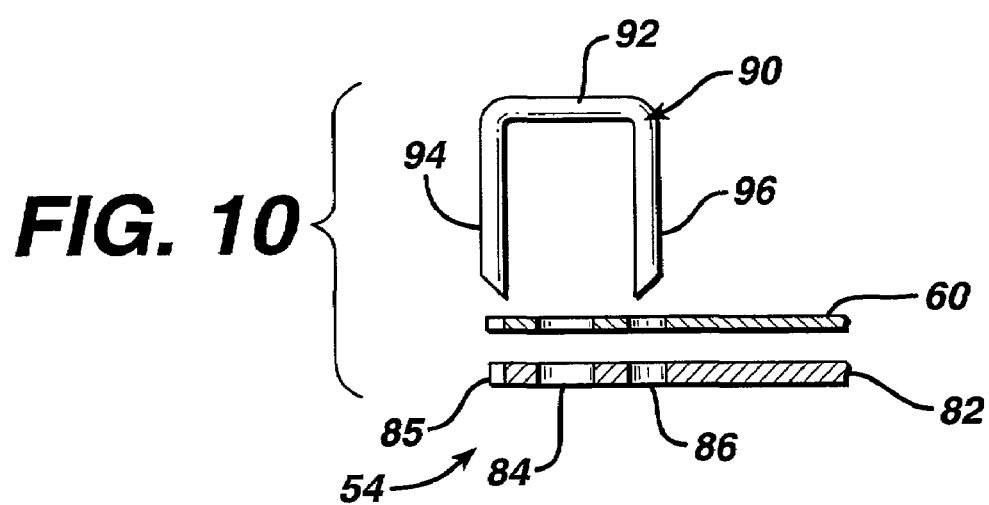
Figure 11:
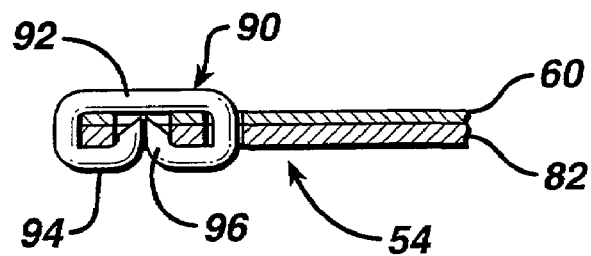

FIG. 9 shows a first connector or proximal attachment connector 54 of a stent, such as stent 40 (FIG. 4). A hoop may include a tab 82 having a first aperture 84 and a second aperture 86, and preferably including a notch 85 or the like at an end opposite the strut. Tab 82 may be a separate element configured to engage a stent, or, as illustrated, may be formed of the junction of two struts 44a and 44b respectively. In the exemplary embodiment of the invention shown in FIGS. 9–11, tab 82 is configured to receive a staple 90 having a first leg 94 and a second leg 96. First aperture 84 is preferably configured to receive a tip portion of both first leg 94 and second leg 96 of staple 90. Second aperture 86 is preferably configured to allow second leg 96 to pass therethrough. In the exemplary embodiments of the invention that include a notch 85, a portion of first leg 94 opposite the tip engages or cradles in the notch 85. In use, second leg 96 passes through graft material 60, through the second aperture 86 of tab 82, and a tip portion of the second leg is bent into first aperture 84. First leg 94 of staple 90 may be positioned on connector 54 by engaging notch 85. A tip portion of the first leg is bent into first aperture 84. In one exemplary embodiment of the invention, the tip portion of the first and second legs engages and preferably penetrates graft 60. In another exemplary embodiment of the invention, the tip portion of the first and second legs engages but does not penetrate the graft 60.

In accordance with preferred embodiments of the invention, a prosthesis may be matingly engaged to another prosthesis using a connector having a nub or spherical end. Exemplary connectors for this aspect of the invention include but are not limited to a rivet, staple, suture, or combinations thereof. An exemplary connector assembly for this exemplary embodiment of the invention is shown in FIGS. 17a and 17b.

Figure 17A:
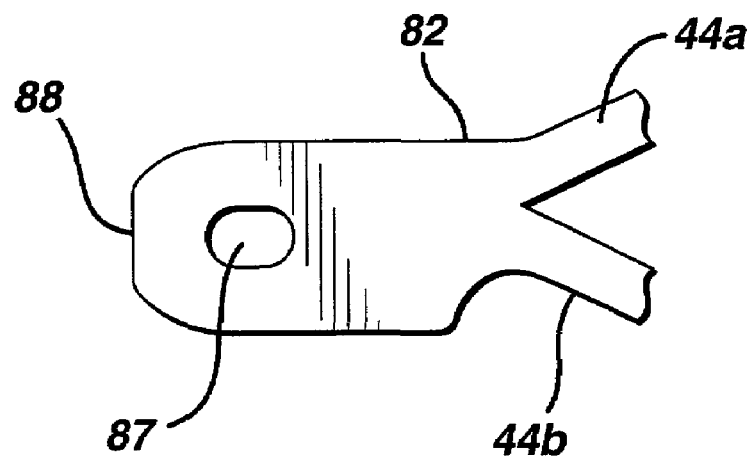
FIGS. 17a and 17b illustrate an alternative connector assembly of the present invention wherein the connector is a suture or the like having a nub or spherical end.

FIG. 17a is an exemplary distal connector on the stent 40 of second prosthesis 11a, b as illustrated in FIGS. 4 and 5, and an exemplary proximal connector on the stent 40 of third or extension prosthesis 160 (illustrated in FIG. 16). The connector is preferably formed from a tab 82 or the like at the junction of two struts, 44a and 44b. Tab 82 includes an aperture 87 near the end 88 of the tab opposite the struts, said aperture being configured to receive a rivet, suture or staple 90 (FIG. 10), or the like.

Figure 17B:
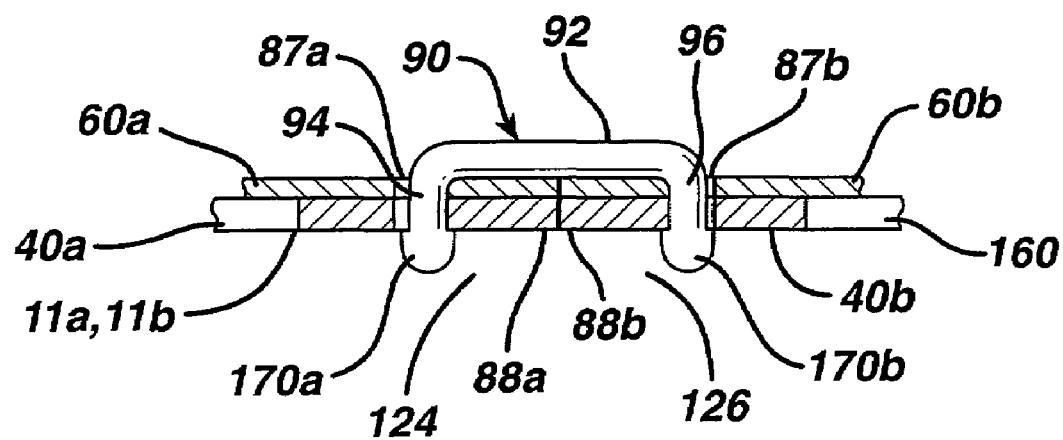

FIG. 17b shows the mating engagement of the second prosthesis 11a, b and the third prosthesis 160. As illustrated, second prosthesis 11a, b includes a distal end 88a having a graft material 60a covering an interior surface of stent 40a. The third prosthesis 160 includes a proximal end 88b having a graft material 60b covering an interior surface of stent 40b. After ends 88a and 88b are aligned, a portion of suture/staple 90 or the like is passed through aperture 87. In the illustrated embodiment, suture/staple 90 includes a crown 92 that bridges an interior surface of prosthesis 11a, b and prosthesis 160. The suture/staple 90 includes a first leg 94 that passes through aperture 87a and a second leg 96 that passes through aperture 87b. Once the suture and prostheses are aligned and in place, the tip of first leg 94 and second leg 96, distal from the crown 92, and positioned on an interior surface of struts 40a and 40b, may be configured into a nub or spherical element 170a and 170b. It should be evident to one skilled in the art that the nub should be of a larger diameter than the diameter of the aperture. In a preferred embodiment of the invention, nubs 170a and 170b may be formed by melting the respective tips.

The present invention also includes an alternate exemplary embodiment for connecting the second prosthesis with the third prosthesis. In this alternate exemplary embodiment (not illustrated), apertures 87a and 87b are aligned and a rivet having two tips is passed through the aligned apertures. Each tip may then be configured into a nub or the like, as described above. In this embodiment of the invention, second prosthesis is matingly engaged to a third prosthesis using one or more rivets that are barbell shaped once the nubs are formed.

Figure 12:
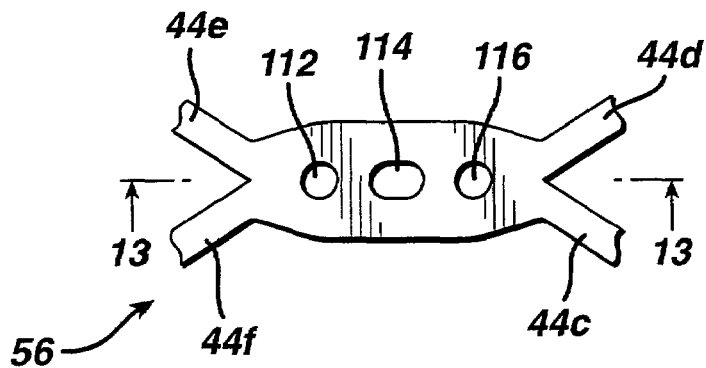
FIGS. 12 through 14 show an alternative connector assembly of the present invention intended for use on an intermediate portion of a stent or prosthesis.
Figure 13:
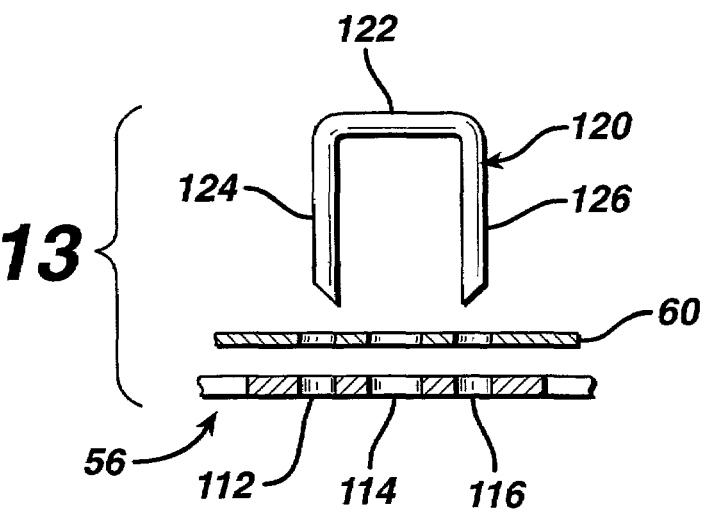
Figure 14:
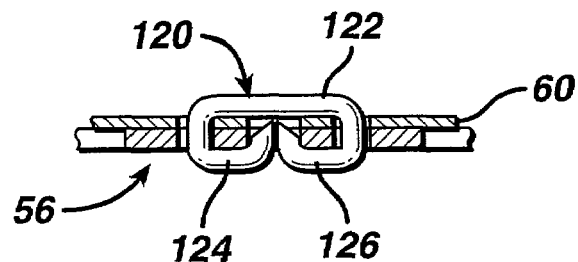

The structures and functions of the second connector 56, illustrated in FIGS. 12–14, are similar or the same as those described above for the first connector. However, in a second connector configuration, the tab also includes a third aperture 112, preferably configured to allow the first leg 124 of staple 120 to pass therethrough. In use, first leg 124 and second leg 126 pass through graft material 60, first leg 124 passes through third aperture 112 and second leg 126 passes through second aperture 116, and a tip portion of each of the first and second legs are bent into first aperture 114. In one exemplary embodiment of the invention, the tip portion of the first and second legs engages and preferably penetrates graft material 60. In another exemplary embodiment of the invention, the tip portion of the first and second legs engages but does not penetrate the graft 60. The second connector 56 is utilized with struts 44c, d, e, f.

The number of connectors and staples are typically dictated by the size and structure of a particular stent; it is intended that the invention should not be limited thereby. The illustrated embodiments show six first connectors and three second connectors.

The above staple aperture design or connector assembly has many advantages for attaching gasket material or a graft material to a stent. Because the legs of the staple are folded around and imbedded within a pocket or the like, any risk of puncturing an inflation balloon is minimized. In addition, the structural integrity of the prosthesis is increased because staples more securely attach the graft material to the stent, as compared to prior art designs which use suture or adhesives to attach the graft to the stent.

Staples 90 and 120 can be made from any number of materials known in the art, including tantalum alloys, platinum alloys or stainless steel, such as a grade of type 316 stainless steel. The staples may take on other configurations and shapes, and can be coated for lubricity purposes, wear resistance and for the prevention of corrosion. Essentially, the coating may be used for increased durability. The staples may be formed from a radiopaque material to identify the location of the staple, and to act as a marker to identify the location of a portion of the prosthesis. Using a different number of radiopaque staples on a distal end of a stent as compared to a proximal end further assists in identifying the position of the prosthesis.

Methods

A method in accordance with the present invention includes delivering and positioning a first prosthesis in a fluid conduit, such as an aorta. In preferred embodiments of the invention, the first prosthesis is a stent gasket, even more preferably, a stent gasket that expands automatically against the wall of the artery. As the stent gasket expands, proximal longitudinal legs allow the stent gasket diamond rings to expand, thereby anchoring the stent in place. The method also includes delivering and positioning at least one second prosthesis. In preferred embodiments of the invention, the second prosthesis is a bypass conduit for extending through an aneurysm. The second prosthesis is typically positioned within the first prosthesis, preferably into and through a hole in the first prosthesis cover. In most preferred embodiments of the invention, the hole is slightly smaller in diameter than the expanded diameter of the second prosthesis, thus sealingly engaging the second prosthesis in the first prosthesis. The sealed configuration of the second prosthesis within the first prosthesis forms a fluid pathway through the assembly or system, thereby bypassing the aneurysm.

Figure 7:
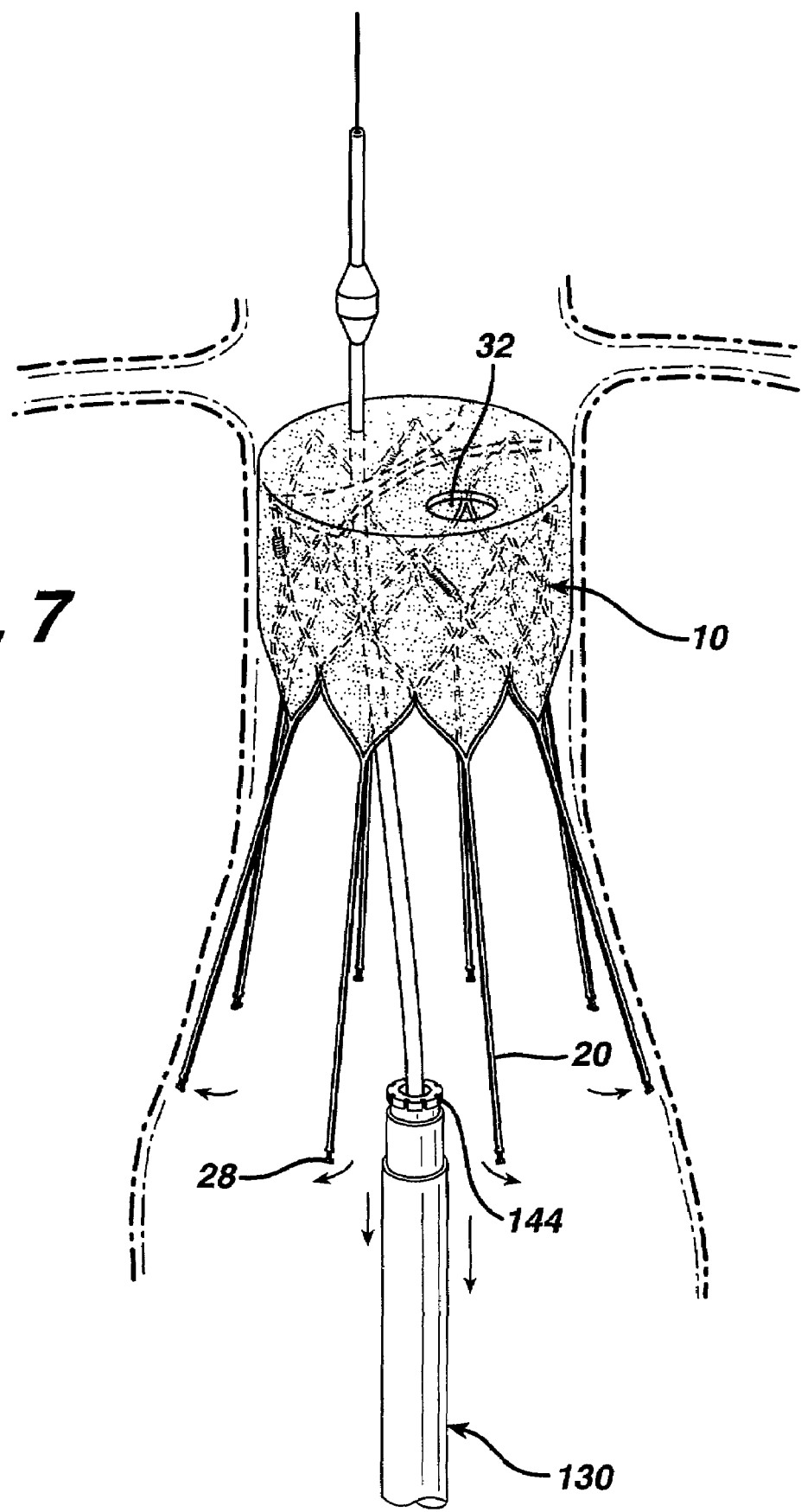
FIG. 7 is a perspective view of a fully deployed first prosthesis made in accordance with the present invention and an exemplary delivery system.

FIGS. 1, 7, and 15 generally show how the system of the present invention may be deployed in vivo. One skilled in the art will readily recognize that a typical delivery device, such as a catheter, includes a guidewire or the like that passes through an aperture in the cover of the first prosthesis, and a collar or the like that releasably engages at least one anchor on the prosthesis. Once the anchors are released from the collar, the first prosthesis can expand, preferably automatically. The portion of the delivery device containing the collar can then be removed from the artery, typically leaving the guidewire in place, i.e., still positioned in an aperture of the first prosthesis cover. The guidewire can then be used to guide a second prosthesis into position within the first prosthesis.

In some exemplary embodiments of the present invention, the collar of the delivery device, engaged to the prosthesis, may be positioned within a sheath or the like until the prosthesis is delivered. In preferred embodiments of the invention, a portion of the prosthesis may be partially deployed and/or positioned. Once it is determined that the prosthesis is in its proper position, the collar can be pushed out of the sheath, thereby releasing the anchors from the collar. If the prosthesis is a self-expanding prosthesis, release of the flanges will allow the prosthesis to deploy automatically. If the prosthesis is not self-expanding, a deflated balloon or the like may be delivered to the interior of the prosthesis using the guidewire. When the balloon is inflated, it will expand the prosthesis into its fully deployed position, i.e., fully expanded radially In preferred embodiments of the invention, the system is used to bypass an abdominal aortic aneurysm (AAA). A method for treating or bypassing an AAA includes delivering, preferably percutaneously, a first prosthesis or precursor stent, or one of its components (e.g., the gasket member may be delivered separately, if desired). The components of the system are typically delivered through one of the femoral arteries and deployed within the infrarenal neck, between an abdominal aortic aneurysm and the renal arteries of a patient. Once the first prosthesis is properly positioned or re-positioned, the legs and anchors are fully released from the delivery device. The delivery device for the precursor stent may then be removed, without removing guidewire, and another guidewire may be inserted through the other femoral artery and into first prosthesis. If the second guidewire is on the wrong side of the interior of first prosthesis, it will contact the occlusive member and be prevented from easily advancing. The physician may then properly reposition the guidewire through hole 32.

Thereafter each delivery apparatus, each containing a sheathed second prosthesis, is inserted into iliac arteries 1 and 2 by sliding them over the guidewires; each of the two second prostheses are then positioned in the first prosthesis. Thereafter, the second prostheses may be either separately or simultaneously deployed.

After proper delivery, first prosthesis 10 and prostheses 11a and 11b should appear as they do in FIG. 1. First prosthesis 10 along with its attached gasket material 30 is firmly secured within the infrarenal neck 101. The outward force of the second prostheses 11a, b on the precursor stent 10 helps to secure the device within the body. The distal ends of the second prosthesis are firmly attached to the iliac arteries 1 and 2. Thereafter blood will flow from the abdominal aorta 302 above the aneurysm 100, through an exemplary system of the present invention comprising a first prosthesis and two second prostheses 11a and 11b, and into iliac arteries 1 and 2, thereby bypassing the aneurysm 100.

It is important to note that even though self-expanding stents are utilized, balloons may be utilized for tacking them into position if necessary.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A system for bypassing an aneurysm comprising:

a first anchoring and sealing device, including an expandable structure having a substantially cylindrical structure with first and second open ends and a sealing material surrounding the substantially cylindrical structure and substantially covering at least one of the first and second open ends, the sealing material comprising a first material;

at least one bypass prosthesis for bypassing an aneurysmal section of the vessel, the at least one bypass prosthesis extending at least partially into the first anchoring and sealing device, the at least one bypass prosthesis comprising a scaffold and graft material attached thereto, the graft material comprising a second material;

at least one extension prosthesis connected to and in fluid communication with the at least one bypass prosthesis, the at least one extension prosthesis comprising a scaffold and graft material attached thereto, the graft material comprising the scond material; and an extension receptacle positionable on or within at least one of the at least one bypass prosthesis and the at least one extension prosthesis, the extension receptacle including a gasket to create a fluid tight seal between the at least one bypass prosthesis and the at least one extension prosthesis, the gasket comprising the first material and wherein the first and second materials are distinct materials.

* * * * *